United States Patent [19]

Sandstrom et al.

[11] 4,392,236
[45] Jul. 5, 1983

[54] SYSTEM AND METHOD OF MIGRATORY ANIMAL IDENTIFICATION BY FLUORESCENCE SPECTROSCOPY OF ELEMENT CODED IMPLANTED TAGS, AND TAGS USED THEREIN

[75] Inventors: Donald R. Sandstrom, Pullman; Farrel W. Lytle, Seattle, both of Wash.

[73] Assignee: Guardsman Chemicals, Inc., Grand Rapids, Mich.

[21] Appl. No.: 243,820

[22] Filed: Mar. 16, 1981

[51] Int. Cl.³ .................... A01K 61/00; G01N 23/22; G06K 7/12

[52] U.S. Cl. ........................ 378/045; 119/3; 250/271

[58] Field of Search .............. 119/3; 250/271; 128/330; 378/44, 45, 86, 88

[56] References Cited

U.S. PATENT DOCUMENTS

| | | | |
|---|---|---|---|
| 2,957,079 | 10/1960 | Edholm | 378/44 |
| 3,128,744 | 4/1964 | Jefferts et al. | |
| 3,369,525 | 2/1968 | Debrotnic et al. | |
| 3,545,405 | 12/1970 | Jefferts | |
| 3,703,726 | 11/1972 | Stephenson | |
| 3,710,104 | 1/1973 | Pavlik | |
| 3,751,661 | 8/1973 | Packer et al. | |
| 3,820,545 | 6/1974 | Jefferts | |
| 3,859,525 | 1/1975 | Ashe et al. | |
| 4,031,388 | 6/1977 | Morita et al. | |
| 4,136,778 | 1/1979 | Wortman et al. | 378/45 |
| 4,233,964 | 11/1980 | Jefferts | 119/3 |

FOREIGN PATENT DOCUMENTS 1933531 1/1970 Fed. Rep. of Germany ....... 250/271

OTHER PUBLICATIONS

Kunzendorf et al., "Determination of Rare Earth Elements in Rocks by Isotope-Excited X-Ray Fluorescence Spectrometry", *Nuclear Instruments and Methods*, No. Holland Pub. Co., vol. 87, No. 2, pp. 197–203.
Kneip et al., "Isotope Excited X-Ray Fluorescence", *Analytical Chemistry*, vol. 44, No. 14, Dec. '82, pp. 57A, 58A, 60A, 63A, 64A, 66A and 68A.
Article by J. R. Calaprice and F. P. Calaprice entitled "Marking Animals with Micro-Tags of Chemical Elements for Identification by X-Ray Spectroscopy", *Journal of the Fisheries Research Board, Canada*, vol. 27, at pp. 317–330, (1970).

*Primary Examiner*—Eugene LaRoche
*Assistant Examiner*—T. N. Grigsby
*Attorney, Agent, or Firm*—John O. Graybeal

[57] ABSTRACT

Identification of migratory animals, such as adult fish and the like, by means of implanted coded tags, with tag coding involving one or more higher atomic numbered chemical elements in stable, solid form (elements with atomic numbers 40–42, 44–53, 55–60 and 62–83), the elements being identified in the live animal by selective X-ray irradiation of the implanted tag and spectral analysis of the fluorescent X-ray radiation emitted by the tag. Rapid analysis of the fluorescent X-ray radiation to identify the coding element(s) with a high level of confidence is obtained by use of high intensity irradiation and controlled masking to essentially confine the irradiation to only the tag and the animal tissue immediately surrounding the tag and thereby improve the signal-to-noise ratio of the fluorescent X-ray radiation emitted by the coding element(s).

52 Claims, 16 Drawing Figures

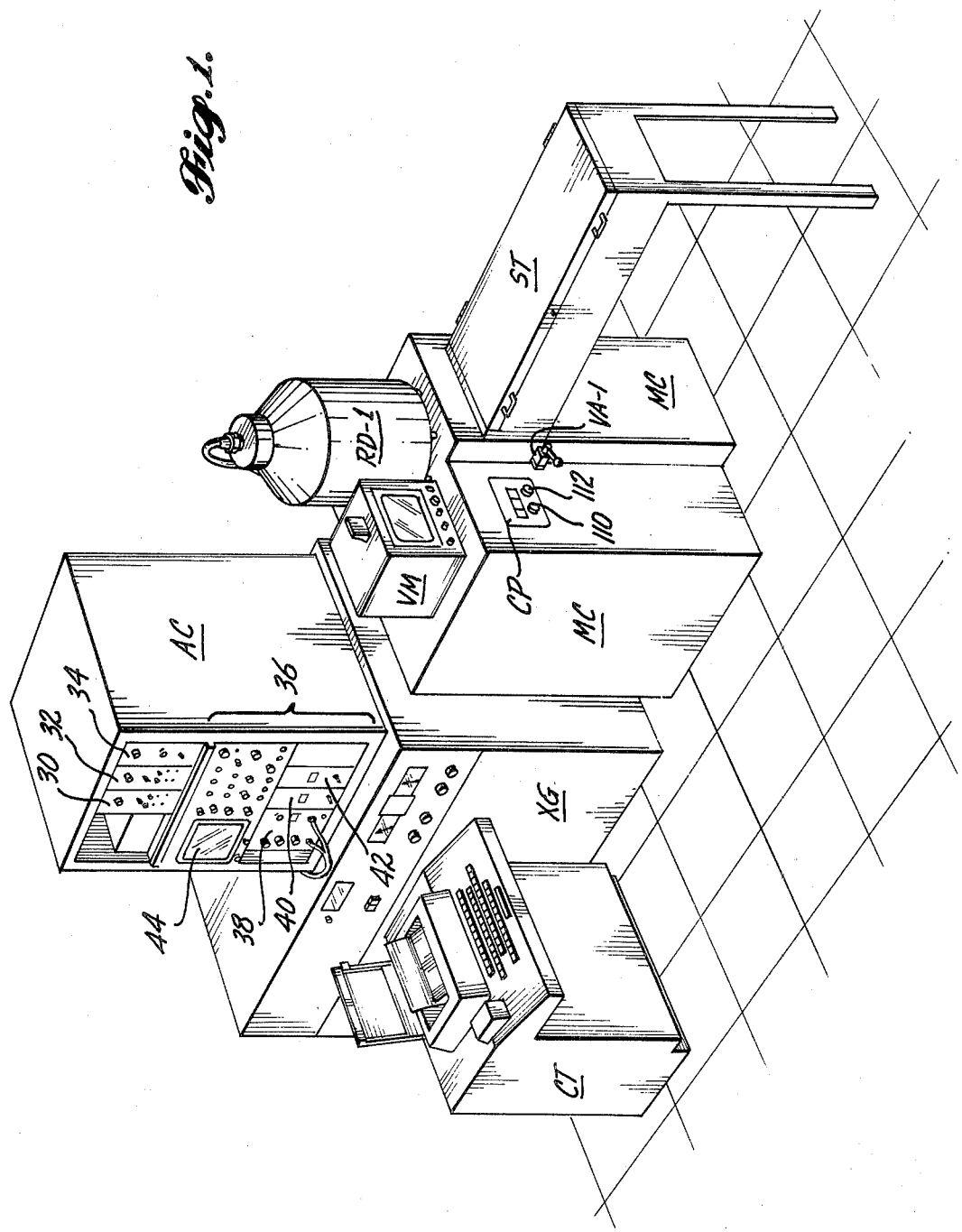

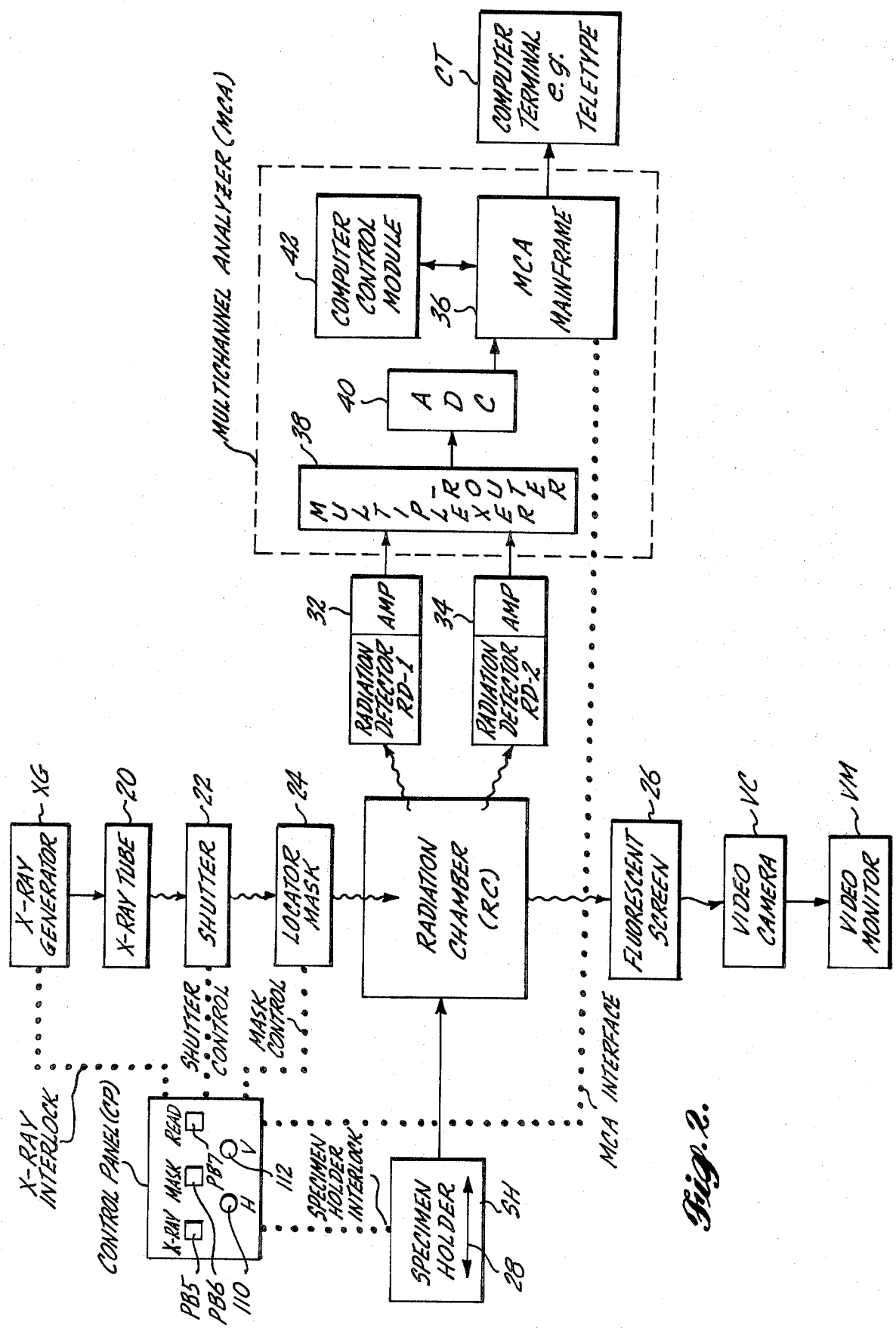

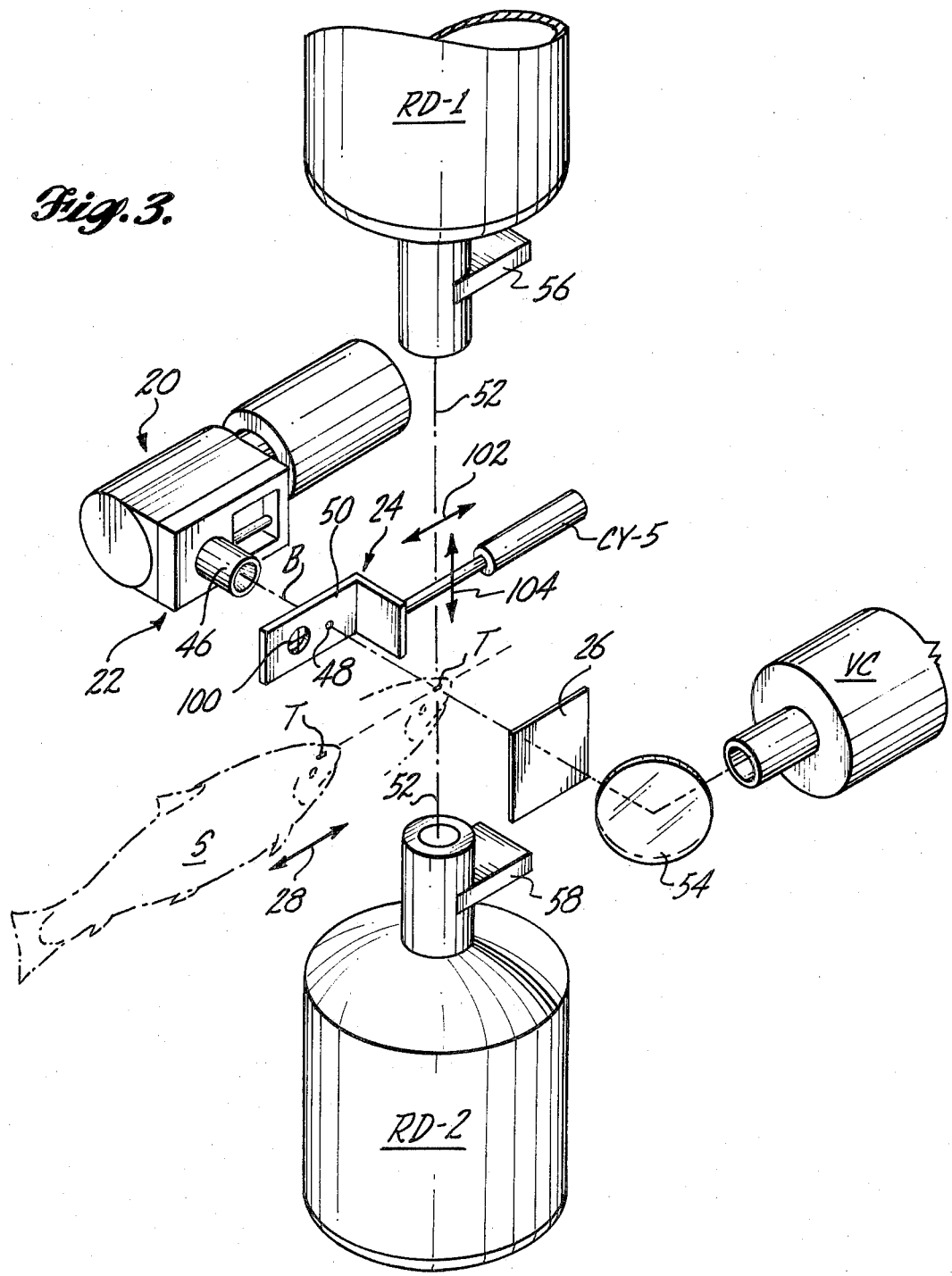

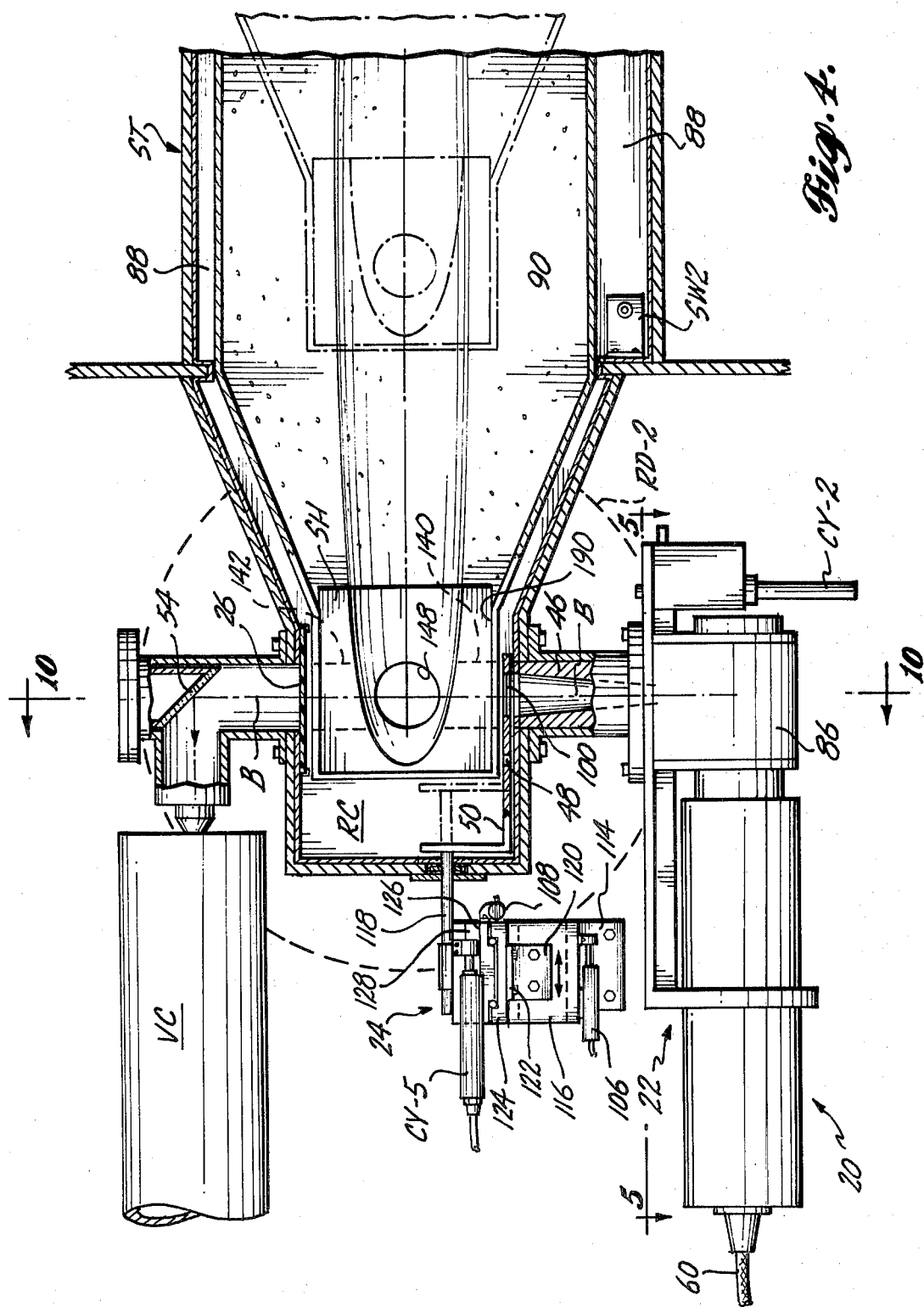

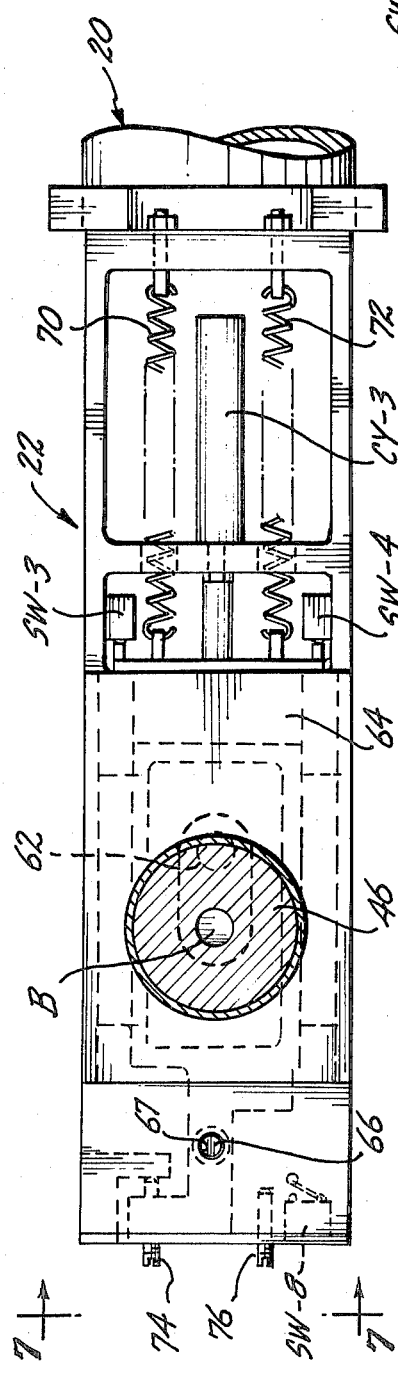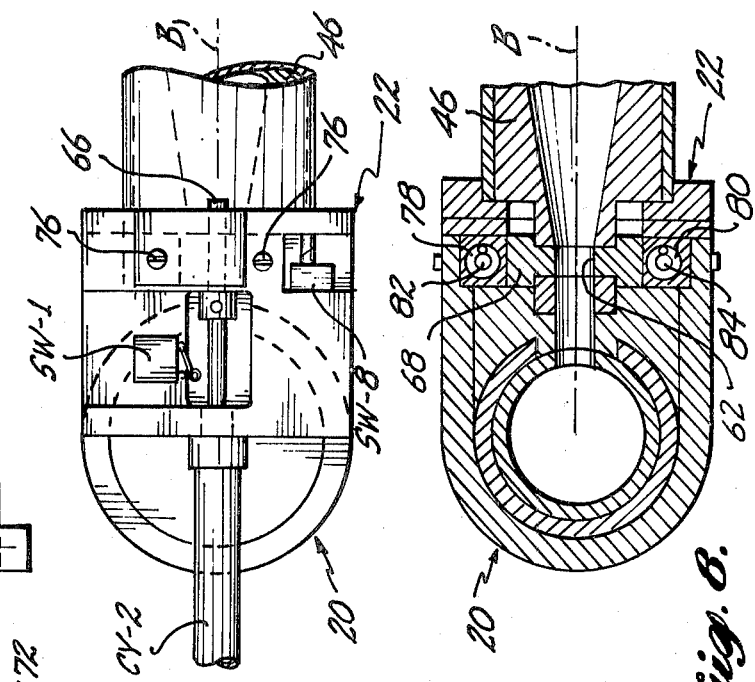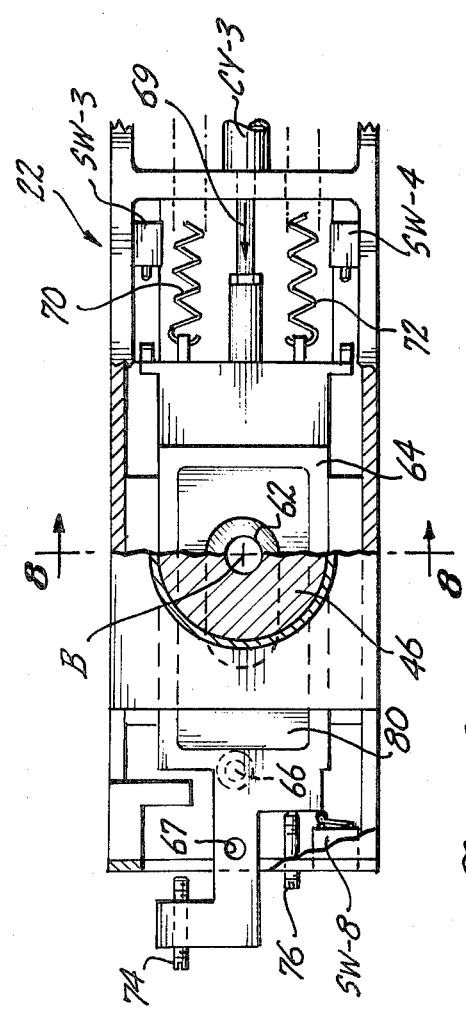

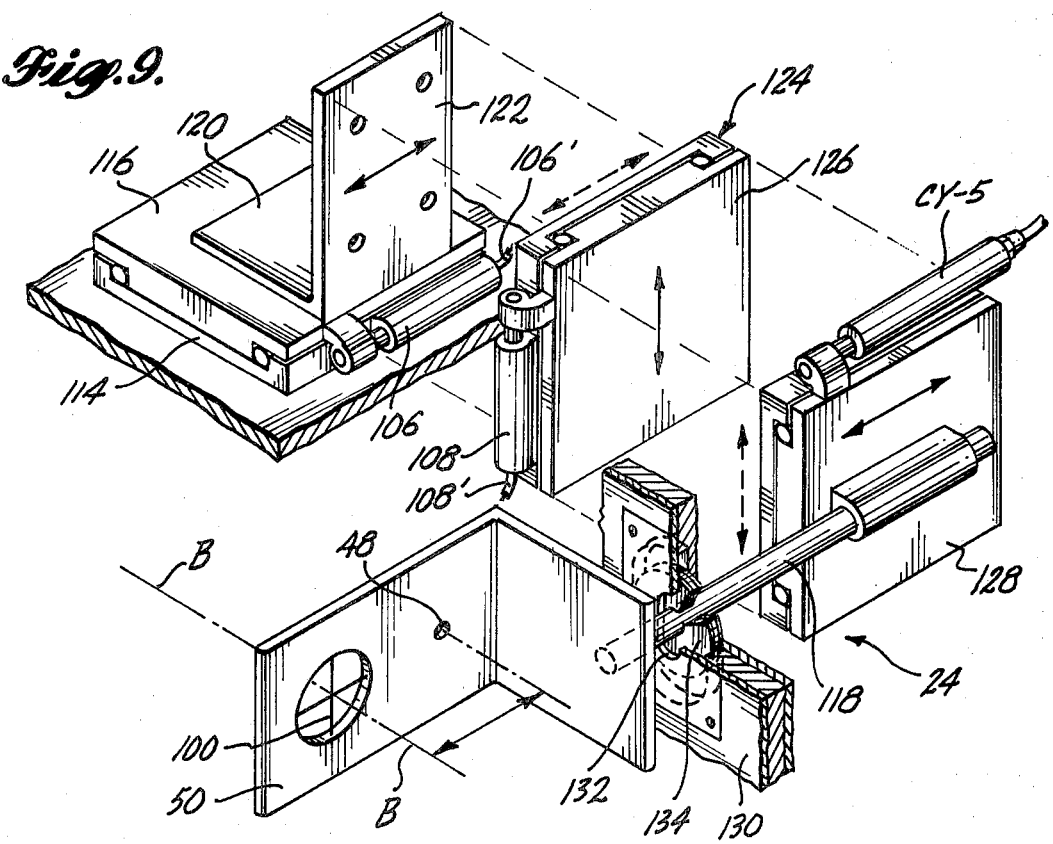
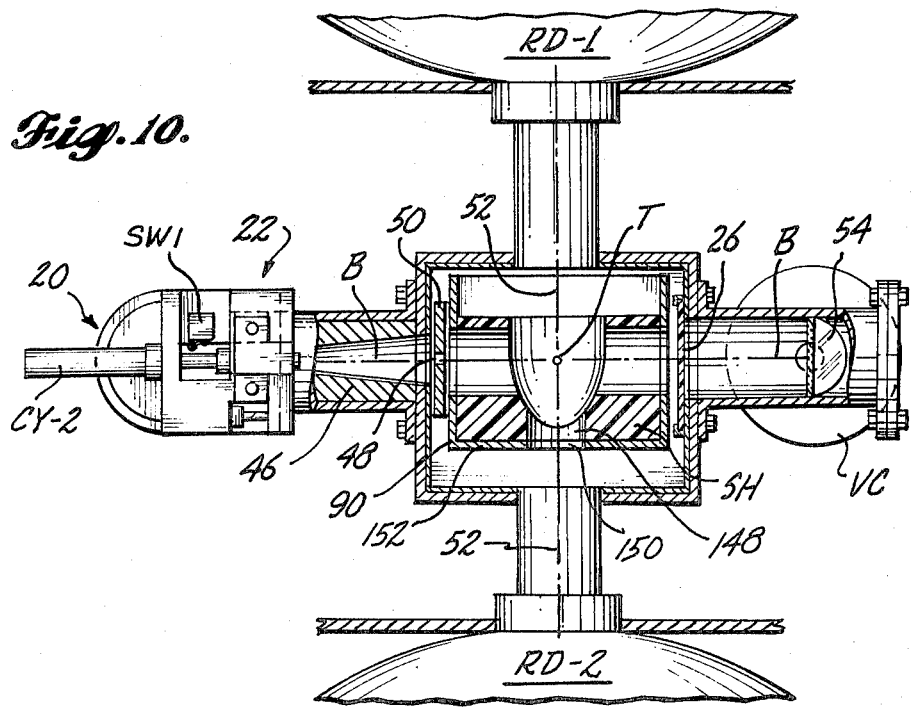

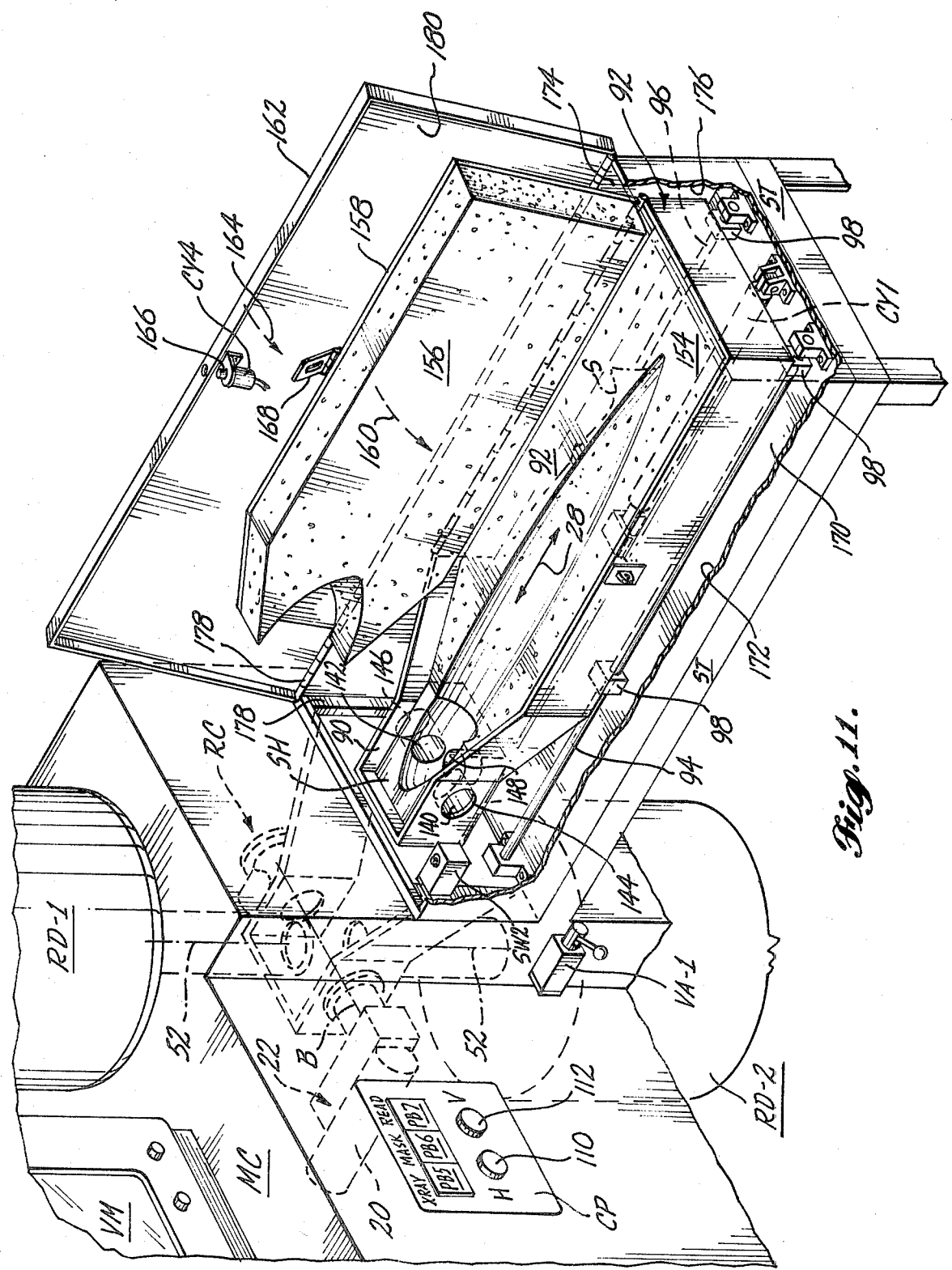

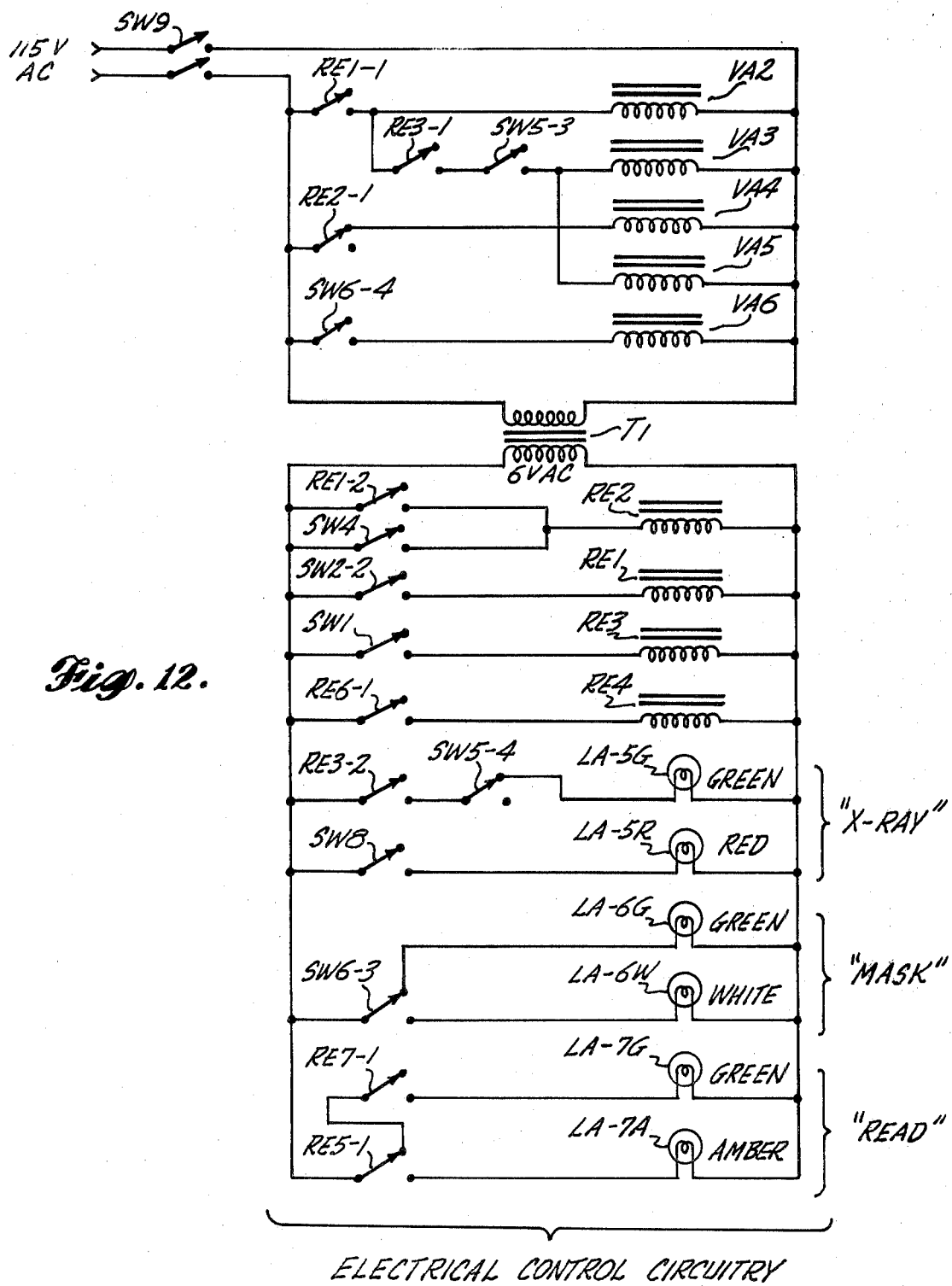

ANALYZER INTERFACE CIRCUITRY

PNEUMATIC CONTROL DIAGRAM

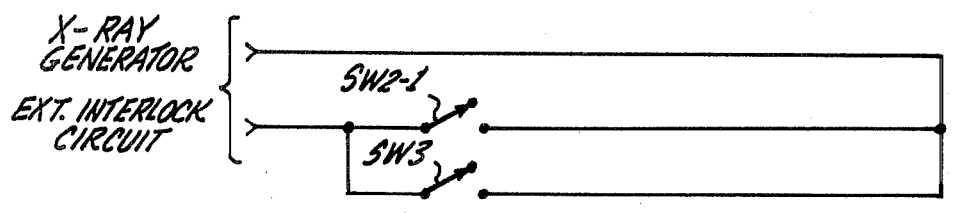
Fig. 15. X-RAY GENERATOR INTERLOCK CIRCUITRY
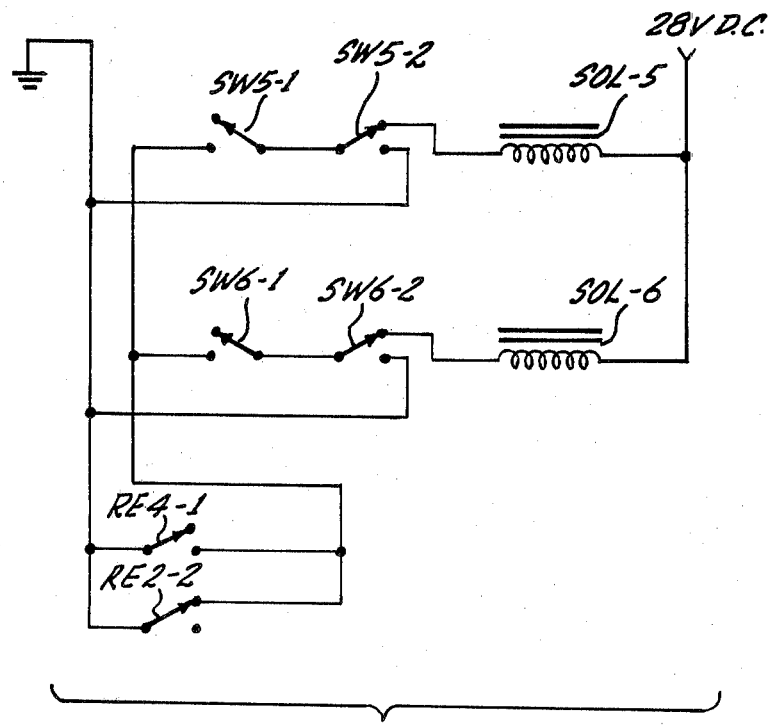
Fig. 16. ELECTRICAL RESET CIRCUITRY

SYSTEM AND METHOD OF MIGRATORY ANIMAL IDENTIFICATION BY FLUORESCENCE SPECTROSCOPY OF ELEMENT CODED IMPLANTED TAGS, AND TAGS USED THEREIN

DESCRIPTION

1. Technical Field

The present invention relates in general to coded tag detection and identification, and more particularly to efficient and accurate identification of chemical element coding in implanted identification tags in adult migratory animals such as adult salmon, such identification being made without harm to the live animal and involving identification tags which can be fabricated and implanted by conventional techniques, and which involve no deleterious characteristics insofar as the utility of the animal for use as food.

2. Background Art

Jefferts et al U.S. Pat. No. 3,128,744 and Jefferts U.S. Pat. Nos. 3,545,405 and 3,820,545, as well as Debrotnic et al U.S. Pat. No. 3,369,525 provide disclosures relating in general to coded identification tags for fish identification and equipments for implanting such tags in fish.

An article by J. R. Calaprice and F. P. Calaprice entitled "Marking Animals with Micro-Tags of Chemical Elements for Identification by X-Ray Spectroscopy" appearing in the Journal of the Fisheries Research Board, Canada, Vol. 27, at pages 317–330 (1970), primarily describes use and analysis of a fish identification tag consisting of mixtures of oxides of chemical elements mixed with silicone rubber and injected just beneath the skin of fingerling salmon (less than 4 inches in length). A method for decoding analysis of the tag by X-ray fluorescence spectroscopy is also described in which a low intensity radioisotope source is used to stimulate emission of characteristic X-rays by the chemical elements present in the tag.

The article presents 30 second, 3 minute and 8 minute spectrograms of fish without tags, fish marked with tags containing no tagging elements, and fish marked with tags containing one, two, or three chemical elements. The article concludes that the tag and method described is suitable for population studies on small salmonoids. The article also makes brief reference (at page 328) of detection of X-ray fluorescence from lanthanum oxide coated magnetic wire tags.

The detection method described in this article is not effective for analysis of tags used to mark live adult salmonoids because adult salmon inherently present a much higher background of scattered X-rays due to the exposure of a much larger volume of tissue to incident radiation when attempting to analyze an embedded tag. Because the resulting higher background X-ray counting levels impose a more stringent requirement on the precision of the X-ray counting measurement, any useful analysis of tags in adult salmonoids demands much higher radiation intensity levels, in terms of count rate per channel in the spectrum region of interest. The analysis method described in this article is essentially quite limited in intensity of incident radiation and counting periods are limited by the requirement of reading tags in live fish, rendering the method described in the article unsuitable for analysis of tags in live, adult salmon. Spectrographs in the article indicate that significant counts per channel for a tagging element were on the order of ten or less for samples exposed for thirty seconds, which is indicative of the fact that the intensity of incident radiation involved in this work was several orders of magnitude less than the radiation intensity characteristic of the system and identification process of the present invention. For comparison purposes, the intensity of the incident radiation characteristic of the irradiation source utilized in the Calaprice et al. system appears to be about $2.6 \times 10^7$ photons/cm$^2$-sec at the identification tag site and without correction for radiation absorption by the surrounding tissue, whereas the intensity of the X-ray radiation employed in the exemplary system here disclosed, by comparable calculation, proves to be about $3.27 \times 10^{10}$ photons/cm$^2$-sec at the tag site, i.e. an intensity about 1200 times greater than the radiation intensity contemplated by Calaprice et al.

Pavlik U.S. Pat. No. 3,710,104 is directed toward analysis of materials for presence of relatively large amounts of specific predetermined chemical elements, distributed relatively uniformly throughout samples presented for analysis during more or less continuous flow. The patent does not provide for detection and analysis of minute quantities of a large number of or combinations of specific elements located only at a specific point or in a small volume within the sample. Classification is according to the presence or absence of chemical elements naturally present in the material being analyzed and is limited to materials or samples containing relatively large concentrations of chemical elements to be identified.

Stephenson U.S. Pat. No. 3,703,726 discloses the method of quantitative chemical analysis of samples by spectroscopic means, the analysis being of the elements inherently present in the sample by reason of the nature of the sample and relies on a more or less uniform distribution of the elements to be analyzed throughout the volume of the sample rather than any attempt to analyze elements concentrated at a discrete point or within a small volume within a sample.

Ashe et al U.S. Pat. No. 3,859,525 discloses a compact, self-contained instrument for quantitative analysis for a single predetermined chemical element. The radioisotope source utilized in this patent disclosure would not provide sufficient sensitivity for detection of microscopic amounts of an element of interest presented for analysis in a large amount of inert material, but relies on a more or less uniform distribution within the volume of the sample of the elements to be detected.

Packer et al U.S. Pat. No. 3,751,661 presents a system for detection of metal wear particles, principally iron, uniformly distributed in liquid oil for monitoring engine performance. Quantitative analysis is provided of a single predetermined chemical element more or less uniformly distributed in this sample.

Morita et al U.S. Pat. No. 4,031,388 describes a method for the quantitative analysis of specific isotopes of chemical elements which by their nature satisfy specific conditions relating to the energy, spin, angular momentum and parity of states of the atomic nucleus and atomic electrons. Specific analysis conditions set forth in the patent render the method insensitive to many chemical elements and many isotopes of chemical elements.

DISCLOSURE OF THE INVENTION

It is an object and feature of the present invention to utilize suitable higher atomic number chemical elements in coded identification tags implanted in adult animals such as salmon, to take advantage of the inherently high fluorescent X-ray radiation energy levels characteristic of these elements so that the radiation attributable to tag coding can escape from the animal tissue in which the tag is embedded. Use of such elements, as hereinafter discussed more specifically, enables use of incident irradiation at high photon energy levels (KeV) for efficient penetration of the host animal tissue while at the same time sufficiently stimulating fluorescent X-ray radiation by the coding elements. Further, the suitable elements are all of nature to be usable in stable, solid form, such as in oxides or like compounds, which compounds are adaptable to incorporation as pigmented coatings on magnetic wire or the like in a manner similar to the conventional fabrication of coded wire tags as discussed in Jefferts and Bergman U.S. Pat. No. 3,128,744 and in Debrotnic U.S. Pat. No. 3,369,525, for example. Further, such elements are not naturally occurring in migratory animals such as fish, and are also advantageous in the sense that in natural form they are nonradioactive so there is no risk of radioactive contamination of the host animal when used as food.

A significant advantage and characteristic of the present invention is that animal identification tags and a coded tag identification system are presented which have the practical capability of rapidly and accurately detecting the presence of code elements in coded tags embedded in adult animals such as spawning salmon, which identification can be made without killing the host animal. Compositely, the factors making this possible are, in general:

(a) use of coding elements having high energy levels of characteristic fluorescent X-radiation, (b) use of high intensity incident irradiation at an energy level efficiently penetrating the animal tissue, (such as 68.8 KeV, which is the energy level of the radiation characteristic of a gold anode X-ray tube) and efficiently causing characteristic fluorescent X-radiation from the coding elements, and (c) use of a masking arrangement to minimize the volume of the specimen exposed to the irradiation and thus minimize the background or scattered radiation without loss of coded element fluorescent X-radiation.

Use of a video radiography system allowing precise positioning of the X-ray beam irradiating the identification tag, and use of energy dispersive spectral analysis for separation and identification of the fluorescent radiation that is produced by the tag for rapid identification of the coding elements, are other advantages of the invention.

It is a further feature of the present invention that live animals can be inspected and processed through accurate identification of an embedded tag in a process or cycle time of sixty seconds or less, which is an important consideration when handling live animals such as adult salmon, since there is substantial risk of loss of or at least harm to the animal if it is out of its natural environment for very long.

It is a further advantage that, utilizing the coding element identification and analysis technique of the present invention, a tangible record of the identification data is made for field record keeping purposes. Yet another advantage and feature is that the system is readily usable by personnel ordinarily involved in fisheries field studies and the equipment is suitable for installation at field sites where fishery studies are ordinarily conducted, such as at dams, hatcheries and the like.

It is another feature and advantage that an operator of the equipment of the invention can immediately determine whether or not an identification tag is present in a given animal specimen by use of video radiography. A further feature and advantage of the identification system of the present invention is that the coding elements involved are incorporatable into magnetic tags of heretofore conventional size and configuration so that conventional tag fabrication procedures and conventional tag implanting equipment continue to be usable therewith.

It is also an object and feature that the equipment is fully suitable for analysis of identification tags which have been removed from specimen animals or which are embedded in preserved specimens or the preserved heads thereof (it being common practice for official fish collection programs to request sports fishermen and the like to turn in specimen heads for tag identification and analysis).

It is also an advantage of the system of the present invention that commercially available components such as an X-ray generator, a multichannel analyzer, video camera and monitor, radiation detectors, and the like, are employed as major components of the system.

It is a further advantage that the analysis of a given identification tag, and the whole operation of the system of the present invention, in the form illustrated and discussed herein, is semiautomated in the sense of being computer controlled, which reduces operator training requirements and also minimizes the period of time during which the animal specimen is exposed to radiation and handling. Computer control also maximizes precision of the analysis to identify coding elements by making possible reliable subtraction of the scattered background contribution to the detected radiation spectrum in the course of determination of the fluorescence radiation associated with coding elements present in a given identification tag.

Yet other advantages and features of the present invention involve the adaptability thereof to identification tag detection and analysis with the tag bearing fish or like specimen alive and alert in its natural habitat, with the tag being located and tracked in three dimensions during irradiation of the tag, as by automatic computer controlled movement of the irradiating X-ray beam responsive to error sensing and servocontrol means, by video raster analysis with computer generated control signals to cause the beam to follow the tag, by ultrasonic sound ranging and/or direction sensing means controlling beam movement, or by electromagnetic sensing of the tag position and responsively controlling beam movement.

For a practical operating standard, it is presently considered that the fluorescent X-ray radiation signal-to-noise ratio during tag identification and analysis should be about four or greater to give a high level of confidence to the anslysis, say 98% confidence. Signal-to-noise ratio is expressed in terms of the number of counts contributed by fluorescence from each coding chemical element alone, which are accumulated in spectral regions of interest associated with the given coding element, divided by the square root of the total number of counts accumulated in the same spectral region. The total number of counts accumulated is contributed almost entirely by background or scattered radiation and only in quite minor part by the fluorescent radiation from a coding element. As used in this context the term "count" refers in the art to the registry in a multi-channel analyzer of a single electrical pulse which in turn is produced by radiation detector means in response to the arrival and detection of a single X-ray photon.

The number of counts attributable to a coding element in any given analysis is proportional to the intensity of the incident irradiation, the mass of the coding element, and the time of irradiation, such proportionality being determined by a constant factor the magnitude of which is determined by the geometry of the radiation components and specimen, the characteristics of the specimen tissue, and the characteristics of the radiation detector means.

The background counts, i.e. the total number of counts accumulated in a spectral region of interest, is proportional to the intensity of incident radiation and the time of irradiation, such proportionality being determined by a constant factor the magnitude of which is determined by the geometry of the radiation components and specimen, the characteristics of the specimen tissue, and the detector characteristics.

It is also to be considered that, as a practical limit, the time of irradiation should be not more than sixty seconds, preferably be about thirty seconds, and optimally be about fifteen seconds or less. A further contributing factor, as earlier indicated, is the mass of coding element present in the tag which is fixed by tag design and which should be at least about 15 micrograms, and preferably at least about 25 micrograms, of each coding element present. Expressed otherwise, the amount of coding element present should be at least about $6 \times 10^{16}$ atoms and preferably at least about $10^{17}$ atoms. Expressed in gram moles, these amounts are at least about $10^{-7}$ gram moles and preferably at least about $2 \times 10^{-7}$ gram moles.

In order to get adequate speed of measurement, i.e. an adequately short cycle time for each coded tag analysis, it is necessary to employ high intensity irradiation, expressed in photons/cm$^2$-sec at the site of the tags, and reflected in a high level of counts per second in each of the different regions of the energy spectrum related to the coding elements of interest. The fluorescent X-ray radiation, as it is detected in the detector means, is a flux of photon particles. Each one of the detected X-ray photons gives an electrical pulse which is recorded in the analyzer as a unit or "count" and the number of units or counts collected in a unit of time is termed the "count rate." The total number of counts accumulated in a given portion of the spectrum determines the precision at which measurements are made and applicable laws of statistics determine how many counts are necessary in order to realize a given level of precision. Most of the counts detected are due to background or scattered radiation. In the tag identification procedure of the present invention background radiation is caused by X-rays having nothing to do with fluorescence of the coding element but are simply generated by scattering processes in the tissue surrounding the specimen and are a useless input to the detector.

In addition to the given level of background radiation that is being continuously detected and counted, at some portions of the spectrum counts are detected which are due to fluorescent X-rays emanating from a coding element or elements in the tag. These wanted or "signal" counts are detected superimposed on the unwanted background counts. To efficiently determine by analysis whether any coding elements are present or not in a given tag, the background counts must be effectively subtracted from the total counts detected, and then a determination made as to whether the remaining or "net" counts add up to a significant number above a zero level.

The magnitude of the background radiation count level to be subtracted can only be estimated to a degree of precision determined by laws of statistics called Poisson statistics. According to Poisson statistics, the degree of imprecision associated with the estimate of the background count level (such degree of imprecision being termed the standard deviation of the estimate) is equal to the square root of the estimated background count level. Upon subtraction of the estimated background count level from the measured total count level, an imprecision which is the same as that of the background count level estimate is contributed to the estimate of net count level. For evaluation of the measurement results, the estimated net count level constitutes the "signal" associated with fluorescent X-rays due to an element in the tag. At the same time the imprecision in the net count level (due almost entirely to the background subtraction) is equivalent to "noise" in the net count measurement.

The presence or absence of a given coding element is determined by examination of the net count level measured for the spectral regions corresponding to the given element. In any given measurement of net count level, the "noise" will contribute positively or negatively in a random manner to the net count level. The confidence with which a positive measurement of net count level can be stated to be due to the detection of fluorescent X-rays due to the given coding element, rather than a randomly occurring positive "noise" contribution can be stated in terms of the ratio of signal to noise. According to the theory of Poisson statistics when applied to counting levels of the order of magnitude encountered in the examples presented, the following relationship exists between the magnitude of the signal-to-noise ratio and the degree of confidence with which a positive net count level for a single element can be attributed to fluorescence X-ray detection and not to noise:

| Signal to Noise Ratio | Confidence Level |
|---|---|
| 0 | 50.0% |
| .5 | 69.1% |
| 1.0 | 84.1% |
| 1.5 | 93.3% |
| 2.0 | 97.7% |
| 2.32 | 99.0% |
| 2.5 | 99.4% |
| 3.0 | 99.9% |

Confidence levels, stated as a percentage number, have the meaning that for a large number of measurements yielding at least a given signal-to-noise ratio, a percentage number of the measurements equal to the corresponding confidence level would be correctly interpreted as being due to fluorescence radiation from the given coding element vs. noise. As an example, if all measurements for a given coding element yielding signal-to-noise ratios equal to or greater than 2.32 are interpreted as being due to the presence of the given coding element, and all measurements yielding less than 2.32 to its absence, the interpretations made will be 99% correct when the test is applied to a large number of measurements.

The signal-to-noise ratio corresponding to a given coding element is determined by the factors described above to be equal to the ratio of the net count level estimate to the square root of the background count level estimate. The following interrelated factors are involved in determining these count levels, and hence the signal-to-noise ratio measured for a given coding element present in the specimen:

(1) Background radiation count level increases in proportion to time of counting;

(2) Background radiation count level increases in proportion to intensity of irradiation;

(3) Net (tag element) radiation count level increases in proportion to time of counting;

(4) Net (tag element) radiation count level increases in proportion to intensity of irradiation.

Hence the signal-to-noise ratio measured for a given coding element present in a given specimen is proportional to the square root of the product of intensity of irradiation times time of counting. It is therefore determined that a required level of signal-to-noise ratio, sufficient to attain a desired confidence level, can be realized in two ways, either by counting for a long time at low intensity of irradiation, or by counting at high intensity of irradiation for a shorter period of time. In practice, short periods of counting are dictated by the limitation on handling time imposed when live animals are to be analyzed, and this consideration leads to the choice of high intensity of irradiation.

A problem associated with the use of high intensity of irradiation to achieve an adequate speed of measurement is that any given radiation detector means can handle only a certain level of incident radiation intensity, reflected in a detector means count rate level at which detector characteristics are distorted and the detector means is said to be saturated. A high intensity X-ray source is readily capable of generating so much background radiation that the detector means is saturated.

Because of these factors it has been found necessary to reduce the background radiation count level as much as possible compared to the coding element fluorescent X-ray radiation count level in order to keep the total count rate at less than the maximum usable intensity level of the detector means without reducing the fluorescent X-ray radiation count level.

The masking procedure adopted in the present invention results in dramatic increase in the signal-to-noise ratios measured for the coding elements because it allows much higher levels of incident irradiation intensity to be used before reaching the level of background count rate at which the detector means is saturated. This results in an increase of net count levels (signal) in proportion to the increase in incident irradiation intensity, with no increase in the background count level (hence no increase in noise).

In general, the chemical elements considered suitable for use as coding elements in practice of the present invention are those higher atomic numbered elements which are naturally occuring and non-radioactive, and which form stable, solid compounds. Such group of suitable chemical elements are the elements from zirconium 40 through bismuth 83 except for technicium 43 and promethium 61 (because these elements are not naturally occurring and are not considered suitable for use as coding elements in view of their radioactive properties) and also except for Xenon 54 (which is an inert gas and does not react to form stable compounds). Elements with atomic numbers below 40 are not considered practical for use as coding elements in practice of the present invention because they have characteristic fluorescent X-ray energy levels which are not sufficiently high to not be unduly absorbed by animal tissue and water surrounding the tag. More specifically, a measure of the penetrating power of fluorescent X-rays emitted by a given chemical element is the path length or thickness of water or tissue through which the fluorescent X-rays, with energy characteristic of the given element, are reduced in intensity by a factor of one-half due to absorption in the water or tissue. In the case of the $K\alpha$ fluorescent X-rays characteristic of zirconium 40, this path length is approximately 0.5 cm. Because of the size and geometry of the specimens involved, this path length is considered to be a practical minimum for reliable tag coding element detection, and since all elements of atomic number less than 40 have corresponding absorption path lengths less than 0.5 cm, zirconium is considered to be the lowest atomic numbered element suitable as a tagging element in practice of the present invention.

Thus, the chemical elements of interest for use as coding elements in identification tags, and the approximate photon energy levels of the $K\alpha_2$ and $K\alpha_1$ fluorescent X-ray radiation characteristic thereof, are as follows:

| Element | Chemical Symbol | Atomic Number | Energy Levels of Interest (KeV)* | |
|---|---|---|---|---|
| | | | $K\alpha_2$ | $K\alpha_1$ |
| Zirconium | Zr | 40 | 15.7 | 15.8 |
| Niobium | Nb | 41 | 16.5 | 16.6 |
| Molybdenum | Mo | 42 | 17.4 | 17.5 |
| Ruthenium | Ru | 44 | 19.2 | 19.3 |
| Rhodium | Rh | 45 | 20.1 | 20.2 |
| Palladium | Pd | 46 | 21.0 | 21.2 |
| Silver | Ag | 47 | 22.0 | 22.2 |
| Cadmium | Cd | 48 | 23.0 | 23.2 |
| Indium | In | 49 | 24.0 | 24.2 |
| Tin | Sn | 50 | 25.0 | 25.3 |
| Antimony | Sb | 51 | 26.1 | 26.4 |
| Tellurium | Te | 52 | 27.2 | 27.5 |
| Iodine | I | 53 | 28.3 | 28.6 |
| Cesium | Cs | 55 | 30.6 | 31.0 |
| Barium | Ba | 56 | 31.8 | 32.2 |
| Lanthanum | La | 57 | 33.0 | 33.4 |
| Cerium | Ce | 58 | 34.3 | 34.7 |
| Praseodynium | Pr | 59 | 35.6 | 36.0 |
| Neodymium | Nd | 60 | 36.8 | 37.4 |
| Samarium | Sm | 62 | 39.5 | 40.1 |
| Europium | Eu | 63 | 40.9 | 41.5 |
| Gadolinium | Gd | 64 | 42.3 | 43.0 |
| Terbium | Tb | 65 | 43.7 | 44.5 |
| Dysprosium | Dy | 66 | 45.2 | 46.0 |
| Holmium | Ho | 67 | 46.7 | 47.5 |
| Erbium | Er | 68 | 48.2 | 49.1 |
| Thulium | Tm | 69 | 49.8 | 50.7 |
| Ytterbium | Yb | 70 | 51.4 | 52.4 |
| Lutetium | Lu | 71 | 53.0 | 54.1 |
| Hafnium | Hf | 72 | 54.6 | 55.8 |
| Tantalum | Ta | 73 | 56.3 | 57.5 |
| Tungsten | W | 74 | 58.0 | 59.3 |
| Rhenium | Re | 75 | 59.7 | 61.1 |
| Osmium | Os | 76 | 61.5 | 63.0 |
| Iridium | Ir | 77 | 63.3 | 64.9 |
| Platinum | Pt | 78 | 65.1 | 66.8 |
| Gold | Au | 79 | 67.0 | 68.8 |
| Mercury | Hg | 80 | 68.9 | 70.8 |
| Thallium | Tl | 81 | 70.8 | 72.9 |
| Lead | Pb | 82 | 72.8 | 75.0 |
| Bismuth | Bi | 83 | 74.8 | 77.1 |

* From "X-Ray Wavelengths", J. A. Bearden, Reviews of Modern Physics, Vol. 39, No. 1, pp. 78–124, January, 1967.

In the examples of practice of the invention here set forth, no specific usage or analysis was made with respect to certain included elements, such as europium, thulium or lutetium in view of cost thereof, although all included elements are deemed demonstrably as operable as the other members of the group and are equally operable and useful if necessary to make up additional coding combinations in a given instance and if the additional cost thereof is justified.

BRIEF DESCRIPTION OF THE DRAWINGS

FIG. 1 is an isometric view of an overall system for practice of the present invention.

FIG. 2 is a block diagram portraying the various components of the system shown in FIG. 1.

FIG. 3 is an exploded isometric view, somewhat schematic in character, showing the interrelation of the active components of the system shown in FIG. 1 which are involved in the irradiation of an implanted identification tag, the detection of radiation emitted therefrom, and the preliminary location and controlled masking of the tag area.

FIG. 4 is a top plan view with various parts broken away and shown in cross section for clarity of illustration, showing the physical layout of equipment components shown in FIG. 3 and the relation thereof to the specimen carriage and specimen holder.

FIG. 5 is a front elevational view taken substantially along line 5—5 of FIG. 4, showing the detail of the X-ray tube shutter assembly with the shutter in its closed position.

FIG. 6 is a further front elevational view, with parts broken away to show further detail, of the X-ray tube and shutter assembly with the shutter in its open position.

FIG. 7 is a further view of the X-ray tube, shutter and beam tube assembly, taken substantially along line 7—7 of FIG. 5.

FIG. 8 is a detail, vertical cross-sectional view taken through the X-ray beam axis, further showing the detail of the X-ray tube, shutter and beam tube, taken substantially along line 8—8 of FIG. 6.

FIG. 9 is an isometric view showing further detail of the mask assembly and the components by which the mask is manipulated.

FIG. 10 is a vertical section through the axial plane including the X-ray beam and detector axes, taken substantially along line 10—10 of FIG. 4.

FIG. 11 is an isometric view, with certain components broken away for clarity of illustration, of the specimen tray, the specimen carriage, and related components of the system shown in FIG. 1.

FIG. 12 is a ladder diagram of the electrical control circuitry employed in the system shown in FIG. 1.

FIG. 15 is a schematic drawing of the X-ray generator interlock circuitry used in conjunction with the control circuit of FIG. 12; and FIG. 16 is a schematic drawing of the electrical reset circuitry used in conjunction with the control circuitry shown in FIG. 12.

BEST MODE OF CARRYING OUT THE INVENTION

Figure 14:
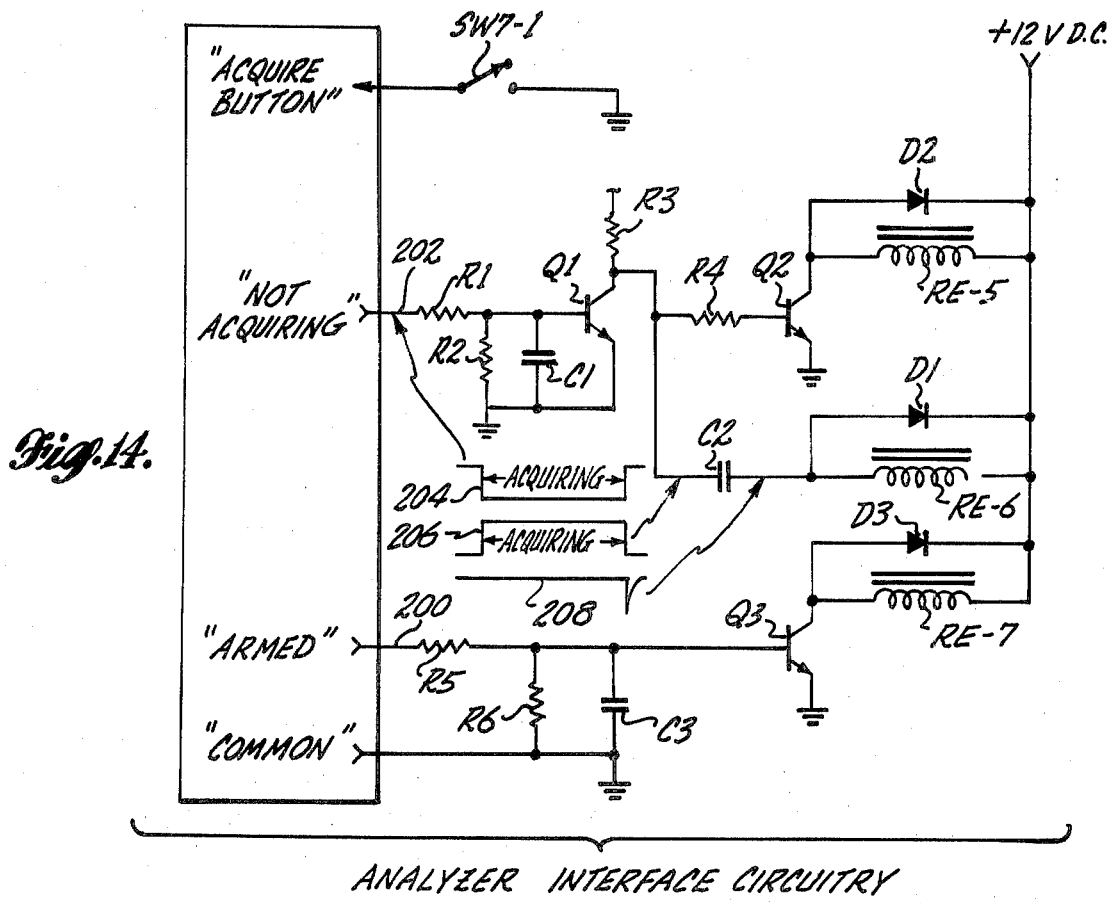
FIG. 14 is a schematic drawing of the multi-channel analyzer interface circuitry.

As shown in FIG. 1, taken in conjunction with the functional diagram presented in FIG. 2, the overall equipment system employed in practice of the present invention in general comprises a main console MC including a control panel CP and on which is mounted video monitor VM and upper radiation detector RD1. Arranged at the front of main console MC is specimen tray ST, shown closed in FIG. 1. Also shown in FIGS. 1 and 2 are X-ray generator XG, the analyzer console AC and the computer terminal CT.

Housed in the main console MC are the X-ray tube 20, the shutter assembly 22, the locator mask assembly 24 and the radiation chamber RC, fluorescent screen 26, video camera VC and the lower radiation detector RD2. Specimen holder SH is shiftable into and out of the radiation chamber RC within the specimen tray ST, as schematically indicated in FIGS. 2 and 11 by arrow 28.

Analyzer console AC houses, in its upper portion, high voltage power supply 30, radiation detector output amplifiers 32, 34 and the multichannel analyzer MCA components including main frame 36 with incorporated modular components including multiplexer/router 38, analog-to-digital converter 40, computer control module 42, and analyzer spectrum display screen 44.

FIG. 3 presents an exploded isometric view of the active components associated with radiation chamber RC. Assuming that a tagged specimen S such as a migratory salmon is at hand, with a coded tag T implanted in its snout, the specimen S is moved on its specimen carriage 92 (FIG. 11) within the specimen tray ST into a position where its tag T is substantially in axial alignment with the axis of the X-ray beam B generated by the X-ray tube 20 and passing through the open X-ray shutter 22, thence through beam tube 46 and aperture 48 of the mask plate 50. Irradiation of the tag T by the beam B causes emission of secondary radiation by the tag T, a portion of which radiation is received by each of the detectors RD1 and RD2 along what is indicated in FIG. 3 as detection axis 52. The irradiation X-ray beam B, in conjunction with the mask aperture 48 and the tag T, form an illuminated area on the fluorescent screen 26 which is reflected by mirror 54 and viewed by video camera VC, the output of which is viewed on video monitor VM by the operator situated alongside the specimen tray ST and control panel CP.

Radiation detectors RD1 and RD2 are respectively of commercially available types such as Model IGP105 and Model IG105, marketed by Princeton Gamma Tech Company of Princeton, N.J., and include built-in preamplifiers as shown in FIG. 3 at 56 and 58, respectively. Detectors RD1 and RD2 are of a type generally known as intrinsic germanium energy dispersive X-ray detectors.

FIG. 4 shows in further detail the mechanical arrangement of the components associated with the radiation chamber RC. The X-ray tube generally indicated at 20 comprises the conventional high voltage input 60 from the X-ray generator XG. As known, X-ray tube 20 emits high intensity X-ray beam B, which passes through opening 62 in plate 64 of the shutter assembly 22 when the shutter is open (FIG. 6). The X-ray shutter assembly 22 includes interlock air cylinder CY2 mounted at the end of the X-ray tube 20 (FIG. 4) which when actuated withdraws interlock latch pin 66 (also see FIGS. 5 and 7). The withdrawal of the latch pin 66 from aperture 67 is sensed by microswitch SW1 (FIG. 7). The operation of shutter interlock cylinder CY2 and microswitch SW1 are further discussed in connection with the electrical control circuitry employed in the system, as are microswitches SW3, SW4 and SW8 (FIGS. 5 and 6). Movement of the shutter plate 64 from beam blocking to beam passing position is accomplished by actuation of air cylinder CY3, which movement is designated by arrow 69 (FIG. 6). Tension springs 70, 72 serve to automatically return the shutter plate 64 to beam blocking position when air cylinder CY3 is not actuated. Respective return motion limiting screws 74, 76 provide means for limiting and adjusting the extent of movement of the shutter plate 64. Shutter plate 64, as shown in FIG. 8, moves on Thompson bearings 78, 80 moving on fixed cylindrical rods 82, 84.

Lead lined housing 86 (FIG. 4) and lead panel 68 in the shutter plate 64, which otherwise is suitably fabricated of stainless steel, together with lead lined beam tube 46, effectively shield beam B from being externally radiated before delivery thereof to the radiation chamber RC. The specimen tray ST is also lead lined throughout, such as indicated at walls 88. The specimen carriage 92 (FIG. 11) into the head end of which the specimen holder SH is placed, is generally indicated at 90 and is described in more detail below.

Mask assembly 24 comprises mask plate 50 which is provided with a cross hair aperture 100 (also see FIG. 3) and small aperture 48. The blade 50 is constructed of Teflon or like coated lead so that the beam B is delivered into the radiation chamber only through one or the other of cross hair aperture 100 or small aperture 48, depending on the position of the plate 50. Plate 50 is reciprocably movable to and from either its tag locator position, with the cross hair aperture 100 in register with the beam axis, or its masking position with its small aperture 48 in register with the beam axis, by actuation of air cylinder CY 5, and is also movable on a vernier basis mechanically both horizontally and vertically, as indicated by respective arrows 102 and 104 in FIG. 3 by means of respective micrometer screws 106, 108 (FIG. 4), actuated through rotation of respective flexible cables 106' and 108' leading to respective horizontal (H) and vertical (V) control knobs 110, 112 on control panel CP. The mounting arrangement by which such movement of the mask plate 50 is accomplished includes a fixed base 114, a rectilineraly movable translation stage 116 permitting horizontal movement in a direction parallel to the length of shaft 118 on which the masking plate 50 is mounted. A mounting bracket 120 provides a vertical face 122 on which a vertically movable translation stage 124 is mounted. Translation stage 124 provides a vertical face 126 to which a horizontally movable translation stage 128 is mounted, the translation of which is limited by and controlled by actuation of air cylinder CY5 and which in turn carries the mounting shaft 118 for the mask plate 50. As shown in FIG. 9, lead lined wall 130 of the radiation chamber RC is apertured as at 132 and includes a floating lead lined Teflon coated plate 134 so there is effective radiation shielding between the interior of the radiation chamber RC and the mask plate mounting mechanism exterior of the chamber.

FIG. 11 shows in isometric, somewhat schematic view with various parts broken away for clarity of illustration, the specimen tray and its included and related components. Within the stationary specimen tray ST, the specimen S is supported and restrained in specimen carriage 92 having a head end 90 which surrounds the specimen holder SH, which suitably is fabricated from resilient synthetic rubber or the like. Carriage 92 is supported to move rectilinearly on stainless steel or like rods 94 and 96 through the medium of Thompson bearings certain of which are shown at 98. Reciprocation of the specimen tray 92 is by means of specimen tray air cylinder CY1 which, for example, has a twelve inch stroke and when extended moves the tray 92 and specimen S from the position shown in FIG. 11 to the position shown in FIG. 4, whereat the tag implanted snout area of the specimen S is substantially in alignment with the axis of beam. As observable in these FIGS. the specimen holder SH is provided with horizontal apertures 140, 142, and the sides of head end 90 of the specimen tray 92 are correspondingly provided with apertures 144, 146 for passage of the beam B horizontally through the tag implanted area of the specimen S, and vertically extending apertures 148, 150 (FIG. 10) are similarly provided in the specimen holder SH and the floor 152 in the head end 90 of specimen carriage 92 to permit passage of the secondary radiation from the tag implanted area of the specimen S downwardly to detector RD2 along detection axis 52, the area above the tag implanted area of the specimen S as shown in FIG. 11 being unrestricted and thus also permitting passage of the secondary detection upwardly along detection axis 52 to upper detector RD1.

Retention of the specimen S in fixed position within the carriage 92 is aided by a lower foam block 154 and an upper foam block 156 carried by tray cover 158 which on being closed as indicated by arrow 160 snugly engages all but the head of the specimen S. Movement of the tray is indicated by arrow 28 (also note FIG. 2).

Stationary specimen tray ST also comprises hinged tray cover 162 which upon closure as indicated at 164 actuates interlock microswitch SW2 which enables actuation of the X-ray shutter air cylinder CY3 as explained in more detail in connection with the electrical control circuitry involved. Said specimen tray cover 162 carries specimen tray cover latch pin air cylinder CY4, the latch pin 166 of which engages with an aperture (not shown, for clarity) in the top edge of the near side of tray ST and locks the cover closed at such time as the operator initiates the radiation sequence by pressing of the X-ray button PB5, also as more fully explained below.

The specimen tray ST, as will be readily understood, is lead lined throughout, including its cover 162, as shown at bottom lining 170, side and end linings 172, 174, 176, 178, and cover lining 180.

The specimen carriage air cylinder CY1 functions to shift the head end of the specimen carriage 92 into and out of the radiation chamber RC. It is actuated by means of double throw air valve VA1 which delivers air from the air supply to one end or the other of air cylinder CY1, either through flow control valve FC1 or flow control valve FC2, each functioning to limit the rate of movement of the specimen carriage 92. As is shown in FIGS. 1 and 11, manually operated air valve VA1 is arranged adjacent the control panel CP and specimen holder SH for easy access by the operator.

Air cylinder CY2 (FIG. 10) extends or withdraws the latch pin 66 which is part of the X-ray shutter 22. The pin 66 when extended serves as a safety interlock, locking the shutter 22 in closed position so it cannot be opened manually, or even on application of air to the X-ray shutter air cylinder CY3 (FIG. 6). The X-ray shutter latch pin air cylinder CY2 (FIGS. 10 and 13) is activated when electrically operated air valve VA2 is energized, which occurs upon energization of relay RE1 through closure of relay section RE1-1 (FIG. 12). Relay RE1 is a double pole double throw relay, which is in turn energized by closure of microswitch SW2 section SW2-2, which switch SW2 (FIG. 11) is closed by closure of the specimen tray cover 162. Switch SW2 is a double pole double throw switch, the other section SW2-1 of which is in an X-ray generator external interlock circuit (FIG. 15). Thus, in terms of the sequence occurring upon closure of the specimen tray cover 162, the microswitch SW2 is engaged, closing its normally open contact section SW2-1 to enable the X-ray generator interlock circuit and closing its switch section SW2-2 to energize relay RE1, the closure of normally open contact section RE1-1 in turn actuating air valve VA2 to deliver air from the air supply to X-ray shutter latch pin air cylinder CY2 which withdraws the latch pin 66, placing air cylinder CY2 which withdraws the latch pin 66, placing the X-ray shutter 22 in "armed" condition, which shutter does not actually open, however, until a subsequent control sequence is initiated, as discussed below.

The operator of the equipment has available to him at the control panel three control pushbuttons PB-5, PB-6 and PB-7 (FIG. 2), respectively labeled "X-RAY", "MASK" and "READ". These respective pushbuttons are each an integral part of and actuate respective modular lighted pushbutton switches SW5, SW6 and SW7 (shown in FIG. 12 by the component makeup thereof), such as Type 2C200 pushbutton switches marketed by Micro Switch Division of Honeywell International. The respective pushbutton switches are also each integrally provided with two condition indicator lights, green light LA-5G and red light LA-5R in the instance of the "X-RAY" button PB-5 and switch SW5, green light LA-6G and white light LA-6W in the instance of switch SW6 and its "MASK" button PB-6, and green light LA-7G and amber light LA-7A in the instance of the "READ" button PB7 and its switch SW7. Switches SW5 and SW6 are four pole double throw type having three switch sections of the alternate action type, and one section of the momentary contact type (e.g. Micro-Switch switch module 2D162) and are either manually actuated by pressing of the respective associated "X-RAY" or "MASK" control buttons PB5 or PB6 or electrically actuated by energization of a solenoid coil, commonly termed a pull-in coil, such coils being designated SOL-5 in the instance of switch SW5 and SOL-6 in the instance of switch SW6 (FIG. 16). Switch SW7, associated with the "READ" button PB-7 is manually actuated, of a type such as Microswitch switch module SD100, with a single momentary contact section SW7-1 (FIG. 14).

Returning to the control condition resulting from the control sequence above described, green light LA-5G is energized to illuminate the "X-RAY" button PB-5 upon withdrawal of the X-ray shutter latch pin 66 and the arming of the X-ray shutter 22. This energization occurs by the mechanical withdrawal of the latch pin being sensed by microswitch SW1 which in turn energizes relay RE3 to close relay contact section RE3-2 and energize lamp LA-5G through normally closed switch contact section SW5-4.

To initiate irradiation of the specimen to determine whether the specimen bears a coded tag and to initiate the sequence for code identification, the operator next manually presses the "X-RAY" button PB5 which shifts the condition of its alternate action contact sections SW5-1, SW5-3 and SW5-4 and momentarily shifts the condition of the momentary contact SW5-2 thereof. Change of condition of contact section SW5-4 interrupts the energization of green light LA-5G. Change of condition of contact section SW5-3, in circuit with previously closed contact section RE3-1 of relay RE3, results in energization of air valve VA3 in the air supply circuit for X-ray shutter air cylinder CY3, and also air valve VA5 in the supply circuit for the specimen tray cover latch pin air cylinder CY4.

Air valve VA4 is provided as a bleed valve in the air supply circuit for shutter air cylinder CY3 and functions as a safety interlock. When it opens to atmosphere upon energization it opens the air supply circuit for the shutter air cylinder CY3 and in such condition maintains the shutter closed. Energization of air valve VA4 to provide the safety interlock occurs upon accidental or improper opening of the specimen tray cover 162, which opening is sensed by microswitch SW2, which in turn de-energizes relay RE1. De-energization of relay RE2 will occur if both microswitch SW4 and relay contact RE1-2 are open (FIG. 12), which condition indicates simultaneous opening of the specimen tray cover and an open condition of the beam shutter 22. De-energization of relay RE2 results in the closing of the contact RE2-1, which energizes valve VA4 and disables the air supply circuit for shutter air cylinder CY3.

As earlier observed in the cylinder CY4, relay contact section RE1-1 is closed through closure of switch contact SW2-2 by closure of the specimen tray cover and relay contact section RE3-1 is closed by actuation of microswitch SW1, indicating the withdrawn condition of the X-ray shutter latch pin 66. With these interlock contact sections closed and with switch contact section SW5-3 in the position for activation of air valve VA3, air is delivered from the air supply through flow control valve FC4 to the X-ray shutter air cylinder CY3 to open the shutter 22. Parallel energization of air valve VA5 delivers air to the air cylinder CY4, which functions to mechanically lock the specimen tray cover 162 closed. The additional contact sections of switch SW5, namely alternate action contact section SW5-1 and momentary contact section SW5-2 (FIG. 16), are in a circuit which performs a reset function at the end of the operation cycle and are discussed subsequently in this connection.

Movement of the X-ray shutter 22 to its open position by actuation of X-ray shutter air cylinder CY3 results in closure of microswitch SW8 which in turn energizes the red lamp LA-5R under the "X-RAY" button PB-5, indicating to the operator that the X-ray shutter 22 is fully open. At this point the operator can see on the video monitor VM the cross hairs 100 of the mask 24 and an image of tag T somewhere on the screen 26 within the illuminated area, presuming a tag T is present. The operator can then, through manipulation of the horizontal (H) and vertical (V) control knobs 110 and 112 on the control panel CP, mechanically move the mask 24 to the point where the intersection of cross hairs 100 of the mask 24 is centered on the tag image. With the tag T thus located and centered, the operator next presses the "MASK" control button PB-6 to shift the mask 24 from its cross hair position to its small aperture position. Green light LA-6G under the "MASK" button PB6 has in the meanwhile been energized through change in condition of alternate action contact section SW6-3 of switch SW6 existing prior to initiation of the control sequence. The change in condition of this contact section SW6-3, occurring upon the manual pressing of the "MASK" button PB6, interrupts the energization of green light LA-6G and energizes white light LA-6W under the "MASK" button PB6 to indicate to the operator the mask 2 has been shifted to its aperture position. Change in condition of contact section SW6-4, which is also an alternate action contact section, accomplishes the energization of air control valve VA6, delivering air from the air supply through flow control valve FC6 to shift the mask shifting air cylinder CY5 from its initial position with the cross hairs 100 in view to its second position with the small mask aperture 48 in view. At this point the operator visually checks the position of the small mask opening 48 with respect to the tag image by observation of such on the video display of video monitor VM, and can make appropriate adjustments necessary at this point to properly center the tag image in the illuminated circle by appropriate further manipulation of the horizontal and vertical controls 110, 112 at the control panel CP to shift the mask position accordingly. As shown in FIG. 16, switch SW6 has two contact sections SW6-1 which is alternate action in character, and SW6-2 which is momentary action in character, which contacts function in the reset mode in a similar way as contact sections SW5-1 and SW5-2 of switch SW5 and are considered in such context below.

The third control button at control panel CP is the "READ" button PB-7 which manually operates switch SW7 and its contact section SW7-1 (FIG. 14) and, as earlier indicated, contains two lamps, a green lamp LA-7G and an amber lamp LA-7A. Energization of the green lamp LA-7G is indicative to the operator of the multi-channel analyzer MCA being in the "armed" mode and energization of amber lamp LA-7A indicates to the operator that the multi-channel analyzer MCA is in the "acquiring" mode. Prior to the operator pressing the "READ" button PB7, the commercially available multi-channel analyzer MCA used as part of the system conventionally involves mode indicating outputs in the form of DC control voltages, the condition of which depends on whether the analyzer is in the "armed" mode and whether the analyzer is in the "acquiring" mode. These output signals from the analyzer are used in the control circuitry presented (FIG. 14) to energize or deenergize control relays which in turn function to indicate to the operator the mode condition of the analyzer. Specifically, the "armed" mode signal output 200 from the analyzer MCA is applied through a voltage divider R5, R6 to the base of transistor Q3 and the higher control voltage condition existing when the analyzer is in the "armed" mode establishes the transistor Q3 as conductive and energizes relay RE7 which in turn shifts the contact section RE7-1 thereof to energize green lamp LA-7G. Prior to the pressing of the "READ" button PB7 by the operator, the analyzer MCA is in the "not acquiring" mode and signal output 202 from the analyzer, at a higher control voltage in this instance, is applied to maintain transistor Q1 in a conductive condition and transistor Q2 in a nonconductive condition so that relay RE5 is not energized and its contact section RE5-1 maintains the energization of green light LA-7G an amber light LA-7A is deenergized. When the operator pushes the "READ" button PB7 the momentary contact section SW7-1 of switch SW7 is momentarily closed, which initiates the multi-channel analyzer analysis of the secondary radiation spectrum being emitted by the tag T, as such radiation is detected by the detectors RD-1 and RD-2. This control is manifested by the contact section SW7-1 closing in the external circuit in parallel with the "acquire" control circuit (not shown) internally of the analyzer MCA. Because it has been put in the "acquiring" mode, the "not acquiring" signal output 202 from the analyzer shifts to a relatively low voltage level (waveform 204) which change in control voltage output renders transistor Q1 nonconductive and transistor Q2 conductive, which in turn energizes relay RE5. This action shifts the condition of contact section RE5-1 of relay RE5 from its normally closed to its normally open position, interrupting the energization circuit for the green lamp LA-7G and energizing the amber light LA-7A to signify to the operator that the system is in the "acquiring" mode.

The multi-channel analyzer MCA remains in the "acquired" mode for a period preset by the computer program in control module 42 (20 to 30 seconds, for example), and upon initiation of its "acquiring" mode, the mode signal output 202 applied to the transistor Q1 through the voltage divider circuit R1 and R2, also applies the change in signal voltage (waveform 206) to capacitor C2 and to the parallel circuit comprising diode D1 and relay RE6. By action of the shunting effect of diode D1 this increase in control signal voltage is shunted past the relay RE6 so no change in its deenergization occurs. However, at the end of the "acquiring" mode of the analyzer MCA the drop in control signal voltage, signifying return of the analyzer to a "non-acquiring" mode, generates a negative voltage pulse of short duration (waveform 208) across diode D1 and relay RE6, causing the relay RE6 to be momentarily energized. This momentary energization causes momentary change in condition of the normally closed contact section RE6-1 of the relay RE6, which energizes relay RE4 and closing of its contact section RE4-1 connects to ground the normally open alternate action sections SW5-1 and SW6-1, which were placed in closed condition at the time the operator initially depresses the respective "X-RAY" and "MASK" buttons PB5 and PB6 for respective manual actuation of switches SW5 and SW6. Such grounding, also reflected through the respective momentary switch contact sections SW5-1 and SW6-2, momentarily energizes the respective pull-in coils SOL-5 and SOL-6 of switches SW5 and SW6, which in turn, by change in condition of all of the alternate action contact sections thereof to their normally closed condition, results in restoration of all of the control circuitry of the system to the initial condition thereof, ready for removal of the specimen S from the radiation chamber RC and its withdrawal from the tray ST, and ready for placement of another specimen S in the tray ST and initiation of another analysis cycle.

A similar restoration, through operation of the electrical reset circuitry shown in FIG. 16, occurs in the event the safety interlock circuitry including bleed air valve VA4 in the shutter air cylinder CY3 control circuit is energized, i.e. when an accidental condition occurs of the specimen tray cover 162 being open simultaneously with an open condition of the beam shutter 22. This interlock action, wherein relay RE2 is de-energized, results in its contact RE2-2 connecting the energization circuits of pull-in coils SOL-5 and SOL-6 to ground, resulting in reset of the system and restoration of all control circuitry thereof to the initial condition, as described above.

As will be readily understood, the electrical circuitry shown in FIGS. 12, 14 and 16 comprise standard electrical circuit inputs, i.e. a line voltage of 115 volts a.c.

supplied through a line switch SW9, and a 6 volt a.c. energization voltage in the lower portion of the circuitry shown, derived from transformer T1, a 12 volt d.c. energization from a standard 12 volt d.c. power supply in FIG. 14, and 28 volt d.c. energization from a standard 28 volt d.c. volt power supply in FIG. 16.

As will be readily understood, in the analyzer interface circuitry shown in FIG. 14, resistors R3 and R4 are present to provide proper bias levels, and capacitor C1 and C3, and diodes D2 and D3 are present to provide noise immunity, in a manner conventional per se. Examples of component values in the analyzer interface circuitry shown in FIG. 14 are as follows:

| | |
|---|---|
| C1 | .01 microfarad |
| C2 | 100 microfarad |
| C3 | .01 microfarad |
| R1 | 470 ohms |
| R2 | 1000 ohms |
| R3 | 1000 ohms |
| R4 | 10,000 ohms |
| R5 | 470 ohms |
| R6 | 1000 ohms |
| D1 | 1N4001 |
| D2 | 1N4001 |
| D3 | 1N4001 |
| Q1 | 2N3704 |
| Q2 | 2N3704 |
| Q3 | 2N3704 |

Figure 13:
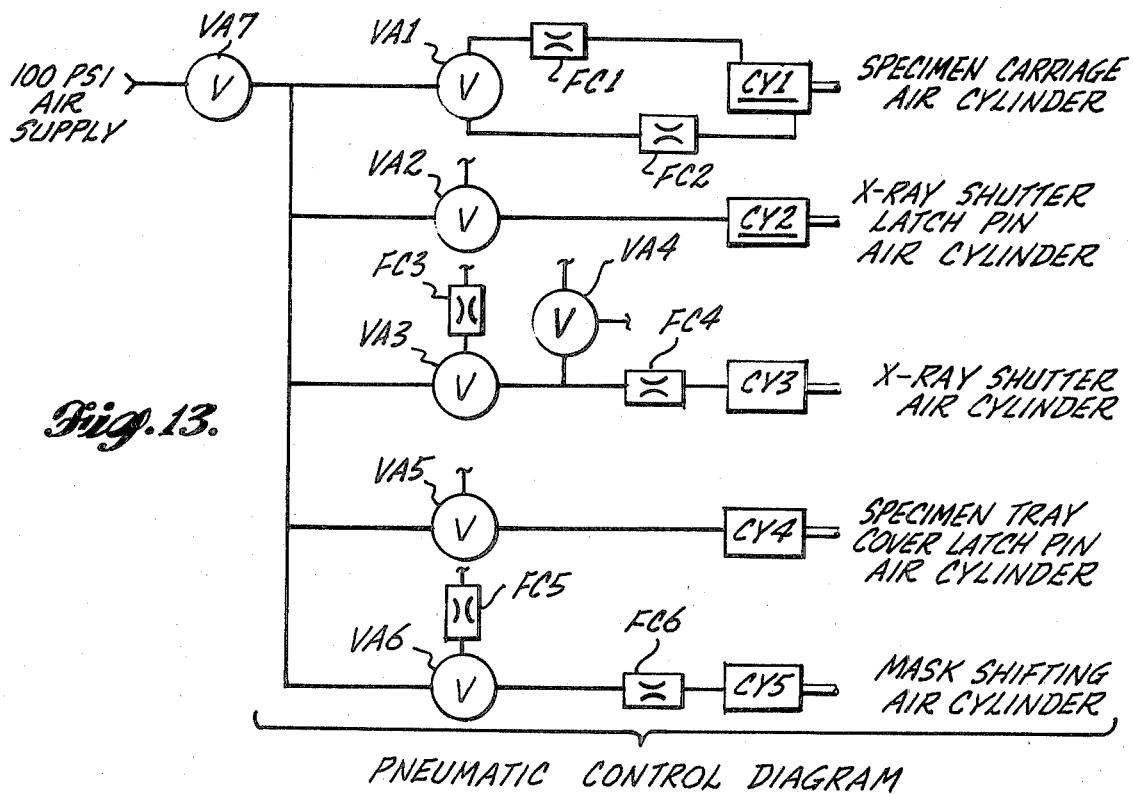
FIG. 13 is a schematic drawing of the pneumatic control circuit.

In the air control circuitry shown in FIG. 13, it will be understood that the air supply from a standard source at appropriate pressure, e.g. 100 psi, is supplied through a standard regulated air valve VA7, and exhaust flow control valves FC3 and FC5 in the exhaust lines of valves VA3 and VA6 are suitably provided to damp the closing action of the respective shutter air cylinders CY3 and mask shifting air cylinder CY5. With reference to the diagrammatic showing of the system layout in FIG. 2, the various interlock and interface components there schematically designated are related to the other components of the overall system as follows. The X-ray generator interlock is made up of the circuitry shown in FIG. 15. The specimen holder interlock is made up of the circuitry and air control for shutter air cylinder CY3, including valve VA4, relay RE2 and microswitch SW4. The analyzer MCA interface circuitry is shown in FIG. 14. The shutter control comprises air valve VA3 and its energization circuitry. The mask control comprises air valve RE6 along with air cylinder CY5 and related control circuitry.

As examples of commercially available equipment usable in the system as disclosed in the foregoing description, X-ray generator XG can be a Philips Electronic Instruments X-ray Generator Model PW1140/96, the X-ray Tube 20 can be a Philips Electronic Instruments tube type PW2181/00, the video camera VC can be a Diamond Electronic Inc. Camera type LL-2, the video monitor VM can be a Conrac Monitor model SNA9/C, the radiation detectors RD1 and RD2 can be a Princeton Gamma Tech Detector Model IG105, the multichannel analyzer MCA can be a Tracor Northern Model TN-1710 equipped with a ADC module 1710-4, a computer control module 1710-45 (Flextran), a calibrator module 1710-8, and an X-ray marker module 1710-13, detector amplifiers 32 and 34 can be Princeton Gamma Tech Amplifier Models 340, and computer terminal CT can be a Teletype Corporation Model ASR-33 teletype.

As an example of practice of the present invention utilized in the equipment as described above, a salmon specimen (Salmo gairdneri species), commonly known as a steelhead, was selected which weighed approximately six pounds and was about twenty-four inches in length. By reason of subsequent testing it was determined that this specimen had been tagged as a fingerling about 18 months previously. The identification tag as implanted in this specimen was a stainless steel tag 0.010 inch in diameter and 0.040 inch long, having a side surface coating of 0.001 to 0.0015 inch thickness containing 34 micrograms of samarium oxide ($Sm_2O_3$), intermixed in cured epoxy resin, the total weight of the coating being 54 micrograms.

Assuming the equipment is in a shut-down condition at the start of the operation cycle, the operator activates the equipment by energizing the power and air supplies. Manufacturers recommended steps are followed to bring the X-ray generator XG up to desired power output level, to activate the multichannel analyzer, and to activate the video monitor VM and video camera VC. Preparation of the multichannel analyzer MCA for analytical use includes inputs of a computer control program and a background radiation spectrum through the computer terminal CT into storage elements which are part of the MCA main frame 36. The background radiation spectrum input is selected to be representative of the background spectrum expected from the type of specimen being analyzed, i.e. a previousy prepared background radiation spectrum evolved from analysis of fish of similar size without an identification tag. In addition, a control program input is made to the MCA mainframe 36 which eventually serves the purpose of semiautomating the analysis operation in that it provides a set of instructions to the computer control module 42 for the analysis sequence.

Assuming proper startup procedure, the "X-RAY", "MASK" and "READ" control buttons PB5, PB6 and PB7 will all be green. Specimen tray cover 162 is then opened, whereupon the "X-RAY" control button PB5 changes from green to a non-illuminated condition. The specimen carriage 92 is retracted (if not already retracted) by actuation of air control valve VA1 and the specimen carriage cover 158 is opened.

The live salmon specimen, after magnetic detection indicative of the presence of a tag and isolation of this specimen in a holding tank, is removed from the tank and anesthetized by immersion in a tank of water to which a suitable anesthetic was added, such as tricane methanesulfonate, also referred to as MS222. Once the specimen is immobile, it is removed from the anesthetizing tank and placed in the form block 154 in the carriage 92, utilizing a substitute specimen holder SH, if the specimen holder SH previously used was other than appropriate size to snugly retain the head of the specimen in a fixed position during the analysis procedure. The head of the specimen is fully inserted in the specimen holder SH, and the specimen carriage cover 158 is closed and latched by latch means 168. With the specimen carriage lid closed, the specimen carriage 92 is moved forwardly, by actuation of air valve VA1, into position with the specimen holder SH fully seated in the radiation chamber RC. The specimen tray cover 162 is then closed, closing microswitch SW2 and restoring the "X-RAY" button PB5 control light to its green condition.

The operator next depresses the "X-RAY" control button PB5 which changes the color display thereof from green to red. At this stage the specimen tray interlock latch pin 166 is extended by actuation of air cylinder CY4 and engages an aperture (not shown) in the near side of the specimen tray ST, and locks the tray cover 162 closed for radiation safety purposes.

A radiographic image of the target cross hairs 100 and the specimen tag T now become visible on the video monitor VM, with the tag T appearing as a dark area or spot on the screen, approximately four times the actual size of the tag. If the tag image is not visible it may either be obscured by the cross hairs 100 image or be off the illuminated portion of the screen, and apropriate manipulation of the vertical and horizontal controls 110 and 112 will bring the tag image to view if a tag is present.

With the image in view and centered on the cross hairs 100 the "MASK" control button PB6 is depressed by the operator, changing its indicator color from green to white, and the tag image then appears on the video monitor VM substantially in the center of the small illuminated area or spot provided by radiation passing through the aperture 48 of the mask assembly 24, which has moved from its first, cross hair display position with respect to the radiation beam RB to its second, aperture display position, through actuation of air cylinder CY5. Any slight off-center condition of the tag image with respect to the center of the aperture display can be corrected by further manual manipulation of the horizontal and vertical controls 110 and 112.

The operator next depresses the "READ" control button PB7, the color condition of which then changes from green to amber and remains amber for the duration of the previously programmed analysis or counting period determined by the analysis control program. In the instance of this example, this analysis or counting period was thirty seconds. At the end of this analysis period all the control panel controls "X-RAY," "MASK" and "READ" buttons PB5, PB6 and PB7 are automatically reset to their "green" condition ready for another operating sequence, and at this point the first operation is complete insofar as irradiation and fluorescent radiation counting are concerned, and latch pin 166, the specimen tray interlock latch pin, is withdrawn so that the specimen tray cover 162 can be opened, the specimen carriage 92 retracted, its cover 158 opened, and the specimen removed. In the case of a live specimen, as in this example, the specimen is promptly placed in a recovery tank and returned to its environment as soon as it revives.

If the next specimen is to be analyzed promptly, it can be immediately placed in the specimen carriage and its operating sequence initiated.

Once the counting period is completed and the outputs from detectors RD1 and RD2 stored in the MCA main frame 36 of multichannel analyzer MCA, the computer control module 42 operates to subtract from the stored counts in each spectrum channel the previously stored background radiation spectrum and also undertakes a so-called refinement step, which is a numerical procedure known per se, the effect of which is to more accurately determine the background radiation for subtraction from the stored spectrum of counts. Part of the computer control program is also, after such subtraction and refinement, the making of a decision as to the presence or absence of given coding elements of interest. Following this analysis and determination as to the presence or absence of coding elements, a numerical printout is generated on the computer terminal CT which, in the instance of this example, was substantively as follows:

| Code Elements | (a) $K\alpha_2$ | (b) $K\alpha_1$ | (c) NET SIGNAL | (d) NOISE | (e) SIGNAL-TO-NOISE RATIO | (f) CODING ELEMENT INDICATOR |
|---|---|---|---|---|---|---|
| CE | 55  | 52   | 107  | 87  | 1.21  | 0 |
| DY | 17  | −134 | −117 | 91  | −1.27 | 0 |
| ER | −15 | 29   | 14   | 103 | 0.13  | 0 |
| GD | −34 | −50  | −84  | 88  | −0.94 | 0 |
| HO | −16 | −184 | −200 | 102 | −1.95 | 0 |
| LA | 33  | 94   | 127  | 86  | 1.46  | 0 |
| ND | −74 | −29  | −103 | 91  | −1.13 | 0 |
| PR | 454 | 716  | 1170 | 89  | 13.07 | 1 |
| SM | −30 | −58  | −88  | 90  | −0.97 | 0 |
| TB | −90 | −67  | −157 | 98  | −1.58 | 0 |
| YB | 94  | −2   | 92   | 103 | 0.89  | 0 | where:
(a) is the net number of counts in the spectrum portion corresponding to the energy of the fluorescence X-rays from the designated element commonly referred to as the $K\alpha_2$ fluorescence emission line;
(b) is the net number of counts in the spectrum portion corresponding to the energy of the fluorescence X-rays from the designated element commonly referred to as the $K\alpha_1$ fluorescence emission line;
(c) is the sum of the net number of counts in the spectrum portions described in (a) and (b), which constitutes the total fluorescence count level detected for the designated element, which count level constitutes the "signal" corresponding to the designated element;
(d) is the square root of the total background radiation count level in the spectrum portions described in (a) and (b), which square root corresponds to the "noise" associated with measurement of the fluorescence count level corresponding to the designated element;
(e) is the ratio of "signal" (column c) to "noise" (column d), which ratio is the signal-to-noise ratio associated with measurement of the fluorescence count level corresponding to the designated element; and
(f) is a binary indication of the analyzer's decision concerning the presence or absence of each of the designated elements, a "1" signifying that the signal-to-noise ratio (column e) is greater than a predetermined decision level value, (four in the first example presented) and an "0" if the ratio is less than the predetermined decision level value.

Thus in this first example presented, the tag is identified as a coded tag and as containing praseodynium (Pr) as the coding element, with no other coding elements present.

The multichannel analyzer employed in the analytical system here disclosed measures all parts of the energy spectrum of the X-rays reaching the detector means simultaneously. The determination of the coded combination of coding elements present in a tapped specimen is then made by separate evaluation of the signal-to-noise ratio associated with each coding element potentially present in the tag. In all but the last series of examples presented eleven elements were potentially present so that a code determination consisted of eleven separate decisions about the presence or absence of each element. In this situation the level of confidence that can be assigned to a complete code determination depends on the signal-to-noise ratio value chosen as a decision level, and on the signal-to-noise ratio measurable, in the average, for coding elements present in a tag. To achieve optimal confidence levels, the decision level for signal-to-noise ratio should be between 3.0 and 4.0 when signal-to-noise ratios of 6.0 or greater are measurable, on the average, for elements present in the tags presented. This assures readout of tag coding combinations at a level of confidence exceeding 98%.

In the following representative further examples, identification tags with the coding element(s) present in total amount of about 30–50 micrograms and in oxide form, were implanted in the snout of an adult steelhead (21 inches in length) and irradiated for 30 seconds in each instance, under like conditions with the equipment above described, with the following results:

| EXAMPLE | S/N RATIO | CODING ELEMENT(S) |
|---|---|---|
| 2 | 7.57 | Pr |
| 3 | 4.08 | Ce |
|  | 12.48 | Pr |
| 4 | 7.50 | La |
|  | 5.34 | Pr |
| 5 | 12.63 | Ce |
| 6 | 9.50 | Ho |
| 7 | 7.51 | Er |
| 8 | 5.36 | Yb |
| 9 | 20.76 | Nd |
| 10 | 9.36 | Gd |
| 11 | 4.00 | Gd |
|  | 11.26 | Tb |
| 12 | 5.96 | Dy |
| 13 | 4.28 | Dy |
|  | 14.92 | Sm |
| 14 | 12.34 | La |
|  | 12.34 | Pr |
| 15 | 10.83 | La |
|  | 4.43 | Nd |
|  | 5.56 | Sm |
| 16 | 6.04 | Gd |
|  | 9.64 | La |
| 17 | 11.64 | La |
|  | 5.73 | Tb |
| 18 | 7.45 | Ce |
|  | 6.80 | Nd |
| 19 | 8.28 | Ce |
|  | 5.63 | Gd |
| 20 | 10.26 | Ce |
|  | 4.43 | Db |
| 21 | 9.45 | Ce |
|  | 5.38 | Dy |
| 22 | 9.96 | Ce |
|  | 4.70 | Er |
| 23 | 10.34 | Pr |
|  | 5.43 | Tb |
| 24 | 13.05 | Nd |
|  | 8.54 | Sm |

To demonstrate the effect of variation in radiation time, the following analyses were conducted under like conditions as Examples 2-24 above, with an identification tag containing about 20 micrograms each of the coding elements La and Pr in oxide form, with the following results:

| Example | S/N Ratio | Coding Elements | Time of Radiation |
|---|---|---|---|
| 25 | 3.67 | LA | 10 sec. |
|  | 6.37 | PR |  |
| 26 | 7.70 | LA | 15 sec. |
|  | 5.51 | PR |  |
| 27 | 5.75 | LA | 15 sec. |
|  | 4.79 | PR |  |
| 28 | 10.29 | LA | 30 sec. |
|  | 8.00 | PR |  |
| 29 | 6.95 | LA | 30 sec. |
|  | 6.02 | PR |  |
| 30 | 10.32 | LA | 45 sec. |
|  | 12.39 | PR |  |
| 31 | 13.05 | LA | 60 sec. |
|  | 12.33 | PR |  |
| 32 | 13.26 | LA | 60 sec. |
|  | 8.56 | PR |  |

To illustrate the scope of the chemical elements usable as coding elements in practice of the present invention, both as to chemical identity and quantity of the element in the tag, the following analyses were conducted under like conditions as involved in Examples 2-24. In addition, in view of the relatively large quantities and the resulting relatively high S/N ratios in most instances, calculations were undertaken as to the equivalent amount of the coding element in each instance which would provide a S/N ratio of 6 when irradiated for 30 seconds. The analyses of these examples yielded the following results:

| EXAMPLE | CODING ELEMENT | CODING ELEMENT ATOMIC NUMBER | CODING ELEMENT QUANTITY | S/N RATIO | EQUIVALENT ELEMENT QUANTITY TO REALIZE S/N = 6; 30 sec. |
|---|---|---|---|---|---|
| 33 | Zr | 40 | 0.30 mg | 30.9 | 58 μg |
| 34 | Pd | 46 | 0.62 mg | 132. | 28 μg |
| 35 | Sn | 50 | 1.8 mg | 336. | 32 μg |
| 36 | Sb | 51 | 1.7 mg | 611. | 17 μg |
| 37 | I | 53 | 1.5 mg | 195. | 46 μg |
| 38 | Cs | 55 | 1.2 mg | 473. | 15 μg |
| 39 | Ba | 56 | 1.9 mg | 620. | 18 μg |
| 40 | W | 74 | 2.0 mg | 24.4 | 490 μg |
| 41 | Hg | 80 | 2.7 mg | 11.6 | 1400 μg |
| 42 | Pb* | 82 | 1.9 mg | 17.7 | 2040 μg |

*Irradiation for 300 seconds in this instance in that the maximum irradiation level available was 100 KV which is near the absorption edge of Pb; a higher irradiation level would enable marked reduction in the necessary irradiation time in the instances of the elements W and above.

While the foregoing examples and system involve tag detection and identification in a live but fully immobilized animal such as a fish, it is also contemplated that variations of the system can evolve which can operate with the fish or the like in the water and active, i.e. can operate on what may be termed a "swim-through" basis. For example, a salmon can be confined or constrained in a channel with water flowing past it, i.e. confined in the sense that the fish is either held or its progress is interrupted by a gate or barrier so it is confined and restricted in its movement but mobile in a segment of a channel during tag irradiation and analysis. In this operating mode the animal is alive, conscious and swimming in its normal attitude and not anesthetized. In such an application of the present invention means would be provided for locating and tracking the tag in three dimensions with the locating and tracking means automatically controlling the application of the X-ray beam to the tag as the fish or the like moves, with the secondary radiation readout taking place in the same way as in the system above described.

Suitable tag locating and tracking means can involve automation of the video radiography locating technique of the system earlier discussed, with the video signal being computer analyzed instead of being displayed on a screen for an operator to intervene, and with the computer analysis being used to automatically control the positioning of the X-ray beam by error sensing and servo control in a manner known per se. Dynamic position of the tag may be sensed by a digital computer analyzing the video picture and generating control signals to cause the beam to follow the tag.

Another suitable tag locating and tracking technique can involve the use of ultrasonic sound ranging and/or direction sensing. For example, by beaming transducer generated ultrasonic sound into the water in which a constrained fish or the like is swimming and locating signal receiving transducers at various angular positions around the animal, directional analysis by computer of the transducer sensed echos can provide a continuing information as to the spatial position of the tag, and this information can be used to maintain the irradiating X-ray beam on the tag.

Electromagnetic tag sensing techniques can also be employed to sense and track the tag in a live and alert but constrained fish or the like. This manner of tag tracking can take advantage of the fact that the tag is metallic and/or magnetic, with tag sensing and location readout by appropriate coils or similar electromagnetic sensors.

Three dimensional tracking of the implanted tag in a live and alert fish or the like is operationally quite desirable from the point of view of improving system performance by increasing signal-to-noise ratio and/or reducing analysis cycle time. Considering that the fluorescent X-ray radiation detection axis is customarily at an intersecting angle (usually perpendicular) to the irradiation beam axis, dynamic point location (rather than line location) of the irradiated tag permits limiting (as by masking) of the field of view of the detector means, insofar as it is sensitive to irradiated matter, specifically to the tag and the animal tissue immediately surrounding it, so that the detector means does not detect scattered radiation from matter in other parts of the irradiating X-ray beam path, with the result that the signal-to-noise ratio of the readout is greatly enhanced.

From the foregoing, various other modifications, adaptations and applications of the present invention will occur to those skilled in the art to which the invention is addressed, within the scope of the following claims.

What is claimed is:

1. The method of identifying the code of an identification tag implanted for a time in the body of a migratory animal, wherein the tag code comprises one or more coding elements including one or more naturally occurring, non-radioactive higher atomic numbered chemical elements in stable solid form and each present in the amount of at least about 15 micrograms, said method comprising:
   (a) irradiating the tag with an X-ray beam at an energy level higher than the absorption edge of any coding element(s) in the tag and at an intensity, disregarding absorptive losses in the animal tissue surrounding the tag, of at least about $3 \times 10^{10}$ photons/cm$^2$-sec;
   (b) masking all but the tag and the animal tissue immediately surrounding the tag from irradiation by the X-ray beam; and
   (c) determining the extent of fluorescent X-ray radiation emitted by any coding element(s) in the tag and from such determination identifying the coding element(s) present in the tag and thus the code thereof.

2. The method of claim 1, wherein at least two said chemical elements are present and identified as coding elements in the tag.

3. The method of claim 1, comprising maintaining the identification tag in fixed position during irradiation thereof.

4. The method of claims 1, 2 or 3, wherein said migratory animal is a fish.

5. The method of claims 1, 2 or 3, wherein said migratory animal is a live adult salmon.

6. The method of claim 1, wherein each such chemical element is selected from the group of chemical elements with atomic numbers of 40-42, 44-53, 55-60, and 62-83.

7. The method of claim 1, comprising radiating the tag with the X-ray beam for about 60 seconds or less.

8. The method of claim 1, wherein the tag is radiated for 30 seconds or less.

9. The method of claim 1, comprising detecting the fluorescent X-ray radiation by multi-channel analyzer means determining the total energy spectrum of the fluorescent X-rays radiated by the tag and the animal tissue and water immediately surrounding the tag, and subtracting from the total emitted energy detected the background radiation emitted from like irradiation of a like specimen and like tag without such coding elements present, to determine what radiated energy is attributable to any coding element(s) present in the tag and thus more readily identify such element(s).

10. The method of claims 1 or 9, comprising identifying any coding element present in the tag on the basis that the net number of counts in the energy spectrum portion corresponding to the energy of the fluorescence X-ray radiation attributable to the coding element results in a signal-to-noise ratio of at least about 4.

11. The method of claim 10, wherein said migratory animal is a fish.

12. The method of claim 11, comprising radiating the tag with the X-ray beam for about 60 seconds or less.

13. The method of tagging a migratory animal with an implanted tag which is coded as to origin, point of release or the like, and subsequently identifying the code of the implanted tag without harm to the animal, said method comprising:
   (a) implanting in the body of the animal an identification tag at least in part including at least one naturally occurring, non-radioactive higher atomic numbered chemical element in stable solid form, each such chemical element serving as a coding element and being present in the amount of at least about 15 micrograms, the chemical element(s) present in the tag providing a coded identification related to the origin, point of release, or the like, characteristic of the animal;
   (b) releasing the animal to its habitat;
   (c) subsequently identifying such animal as being tagged by sensing the presence of the tag within the animal and confining the animal, so identified;
   (d) while the animal is alive, irradiating the tag with an X-ray beam at an energy level higher than the absorption edge of the coding element(s) comprising the tag and at an intensity, disregarding absorptive losses in the animal tissue surrounding the tag, of at least about $3 \times 10^{10}$ photons/cm$^2$-sec;
   (e) masking all but the tag and the animal tissue immediately surrounding the tag from irradiation by the X-ray beam;
   (f) determining the extent of fluorescent X-ray radiation emitted by the coding element(s) in the tag and from such determination identifying the coding element(s) present in the tag and thus the code thereof; and
   (g) subsequently releasing the live animal to its habitat.

14. The method of claim 13, wherein at least two said chemical elements are present and identified as coding elements in the tag.

15. The method of claim 13, comprising maintaining the identification tag in fixed position during irradiation thereof.

16. The method of claims 13, 14 or 15, wherein said migratory animal is a fish.

17. The method of claims 13, 14 or 15, wherein said migratory animal is a live adult salmon.

18. The method of claim 13, wherein each such chemical element is selected from the group of chemical elements with atomic numbers of 40-42, 44-53, 55-60, and 62-83.

19. The method of claim 13, comprising radiating the tag with the X-ray beam for about 60 seconds or less.

20. The method of claim 13, wherein the tag is radiated for 30 seconds or less.

21. The method of claim 13, comprising detecting the fluorescent X-ray radiation by multi-channel analyzer means determining the total energy spectrum of the fluorescent X-rays radiated by the tag and the animal tissue and water immediately surrounding the tag, and subtracting from the total emitted energy detected the background radiation emitted from like irradiation or a like specimen and like tag without such coding elements present, to determine what radiated energy is attributable to any coding element(s) present in the tag and thus more readily identify such element(s).

22. The method of claim 21, comprising identifying any coding elements present in the tag on the basis that the net number of counts in the energy spectrum portion corresponding to the energy of the fluorescence X-ray radiation attributable to the coding element results in a signal-to-noise ratio of at least about 4.

23. The method of claims 21 or 22, wherein said migratory animal is a fish.

24. The method of claim 23, comprising radiating the tag with the X-ray beam for about 60 seconds or less.

25. An identification tag for implanting within the body of a migratory animal or the like, and for subsequent identification by the presence of selected coding elements therein, said tag comprising a generally cylindrical body approximately 0.010 inch in diameter and about 0.040 inch in length, and at least in part including several coding elements selected from the group consisting of the naturally occurring non-radioactive higher atomic numbered chemical elements in stable solid form, said tag having present at least about 15 micrograms of each such chemical element.

26. An identification tag according to claim 25, wherein said tag is in the form of:
(a) a generally cylindrical stainless steel body approximately 0.040 inch in length, with
(b) a surface coating at least about 0.001 inch thick on said body and including several code elements in admixture with a cured epoxy or like resin.

27. An identification tag according to claim 25, wherein said coding elements are selected from the group consisting of the chemical elements having an atomic number of 40 to 42, 44-53, 55-60 and 62-83, with such chemical elements being present in oxide form.

28. An identification tag according to claims 25, 26 or 27, including at least three such coding elements.

29. A system for identifying by X-ray fluorescence analysis any higher atomic numbered chemical elements present as coding elements in a tag implanted for a time in the body of a migratory animal, said system comprising:
(a) an X-ray generator and X-ray beam delivery means producing a beam of X-rays of an energy higher than the absorption edge of the fluorescent X-ray radiation of any coding element(s) in the tag, and of an intensity, disregarding absorptive losses in any animal tissue surrounding the tag, of at least about $3 \times 10^{10}$ protons/cm$^2$-sec;
(b) a system for precisely locating the tag and irradiating the tag with such X-ray beam, and including masking means providing that only the tag and a minimal amount of any animal tissue immediately surrounding the tag are irradiated by the X-ray beam;
(c) energy dispersive X-ray detector means sensitive to the characteristic fluorescent X-ray radiation radiated by any coding element(s) in the tag during irradiation thereof; and
(d) multi-channel analyzer means determining from the radiation detected by said detector means the energy spectrum of the fluorescent X-ray radiation emitted by any coding element(s) in the tag, and thus identifying such coding element(s).

30. The system of claim 29, wherein said masking means comprises a lead or like masking plate arranged generally transversely of the X-ray beam and apertured to provide irradiation of only the identification tag and that portion of the animal tissue surrounding the X-ray beam axis.

31. The system of claim 30, wherein said masking plate is provided with a first, relatively larger aperture for tag location and a second relatively smaller aperture for limiting the effective width of the X-ray beam during analytical irradiation of the tag, and said masking means includes means for vertically and horizontally adjusting each such aperture laterally with respect to the X-ray beam and means for shifting said masking plate to and from respective positions with the beam passing through one or the other such apertures.

32. The system according to claim 31, wherein the means for adjusting each aperture laterally of the X-ray beam is under the normal control of the system operator.

33. The system according to claim 29, wherein said masking means includes a shielding plate with plural apertures, said shielding plate being carried by a horizontally movable translation stage shiftable from one position with one aperture coincident with the X-ray beam to a second position with another aperture coincident with the X-ray beam, said horizontal movable translation stage being in turn carried by a vertically movable translation stage, respectively in turn carried by a second horizontal translation stage, the latter two such stages permitting vernier vertical and horizontal adjustment of the mask apertures with respect to the X-ray beam.

34. The system according to claim 30, wherein the tag locating means comprises radiographic image development means including a fluorescent screen irradiated by the X-ray beam portion passing through an aperture in the masking means, and on which a shadow of the identification tag appears visually.

35. The system according to claim 34, wherein the tag locating system further includes video camera means viewing said fluorescent screen and providing an output displayed on a video monitor viewed by the system operator to enable remote manual manipulation by the operator of the masking means for centering of the tag substantially on the axis of the X-ray beam forming aperture.

36. The system according to claims 29 or 35, further comprising means for holding the migratory animal and its identification tag in fixed position with respect to the X-ray beam during irradiation of the tag.

37. A system according to claims 29 or 35, as applied to identification tag analysis with the tag implanted in the immobile snout of an animal, and further comprising a radiation chamber through which the mask restricted X-ray passes, an animal specimen carriage movable laterally into and out of the radiation chamber and carriage cover means for opening during placement and removal of a specimen animal when the carriage is retracted away from the chamber and closeable for retention of the specimen animal in the carriage during carriage movement into the radiation chamber and during irradiation of the tag in the radiation chamber.

38. The system according to claim 37, comprising interlock means responsive to carriage cover position to prevent X-ray beam delivery into the radiation chamber whenever the carriage cover is open.

39. The system according to claim 29, wherein the energy dispersive X-ray detection means comprises plural detectors arranged substantially perpendicularly of the X-ray beam in the radiation chamber.

40. The system of claim 29, wherein said multi-channel analyzer means is programmed to identify any coding element present in the tag on the basis that the net number of counts in the energy spectrum portion corresponding to the energy of the fluorescence X-ray radiation attributable to the coding element results in a signal-to-noise ratio of at least about 4.

41. A system for rapidly identifying by X-ray fluorescence analysis any higher atomic numbered chemical elements present as coding elements in an identification tag implanted for a time in the body of a live migratory animal, said system comprising:

(a) means for retaining the live animal substantially immobile and in position for radiographic imaging of the tag and for irradiation of the tag by a narrowly defined beam of X-rays;

(b) X-ray generator and X-ray beam delivery means producing a beam of X-rays of an energy higher than the absorption edge of the fluorescent X-ray radiation of any coding element(s) in the tag, and of an intensity, disregarding absorptive losses in any animal tissue surrounding the tag, of at least about $3 \times 10^{10}$ photons/cm$^2$-sec;

(c) a system for precisely locating the tag and irradiating the tag with such X-ray beam, and including masking means providing that only the tag and the animal tissue immediately surrounding the tag and in alignment with the X-ray beam axis are irradiated by the X-ray beam;

(d) energy dispersive X-ray detector means sensitive to the characteristic fluorescent X-ray radiation radiated by any coding element(s) in the tag during irradiation thereof; and (e) multi-channel analyzer means determining from the radiation detected by said detector means the energy spectrum of the fluorescent X-ray radiation emitted by any coding element(s) in the tag, and thus identifying such coding element(s).

42. The system of claim 41, wherein said masking means comprises a lead or like masking plate arranged generally transversely of the X-ray beam and apertured to provide irradiation of only the identification tag and that portion of the animal tissue surrounding the X-ray beam axis.

43. The system of claim 42, wherein said masking plate is provided with a first, relatively larger aperture for tag location and a second relatively smaller aperture for limiting the effective width of the X-ray beam during analytical irradiation of the tag, and said masking means including means for vertically and horizontally adjusting each such aperture laterally with respect to the X-ray beam and means for shifting said masking plate to and from respective positions with the beam passing through one or the other.

44. The system according to claim 43, wherein the means for adjusting each aperture laterally of the X-ray beam is under the manual control of the system operator.

45. The system according to claims 42 or 43, wherein the tag locating means comprises radiographic image development means including a fluorescent screen irradiated by the X-ray beam portion passing through an aperture in the masking means, and on which a shadow of the identification tag appears visually.

46. The system according to claim 45, wherein the tag locating system further includes video camera means viewing said fluorescent screen and providing an output displayed on a video monitor viewed by the system operator to enable remote manual manipulation by the operator of the masking means for centering of the tag substantially on the axis of the X-ray beam forming aperture.

47. The system according to claim 41, wherein said masking means includes a shielding plate with plural apertures, said shielding plate being carried by a horizontally movable translation stage shiftable from one position with one aperture coincident with the X-ray beam to a second position with another aperture coincident with the X-ray beam, said horizontal movable translation stage being in turn carried by a vertically movable translation stage, respectively in turn carried by a second horizontal translation stage, the latter two such stages permitting vernier vertical and horizontal adjustment of the mask apertures with respect to the X-ray beam.

48. The system of claim 41, wherein said multi-channel analyzer means is programmed to identify any coding element present in the tag on the basis that the net number of counts in the energy spectrum portion corresponding to the energy of the fluorescence X-ray radiation attributable to the coding element results in a signal-to-noise ratio of at least about 4.

49. The system according to claim 41, wherein the energy dispersive X-ray detection means comprises plural detectors arranged substantially perpendicularly of the X-ray beam in the radiation chamber.

50. The system according to claim 49, wherein the X-ray detector means is disposed approximately 90° with respect to the beam of X-rays aimed at the tag.

51. A system according to claim 41, as applied to identification tag analysis with the tag implanted in the immobile snout of the animal, and further comprising a radiation chamber through which mask restricted X-ray beam passes, an animal specimen carriage movable laterally into and out of the radiation chamber and carriage cover means for opening during placement and removal of a specimen animal when the carriage is retracted away from the chamber and closeable for retention of the specimen animal in the carriage during carriage movement into the radiation chamber and during irradiation of the tag in the radiation chamber.

52. The system according to claim 51, comprising interlock means responsive to carriage cover position to prevent X-ray beam delivery into the radiation chamber whenever the carriage cover is open.

* * * * *